US006214984B1

(12) United States Patent
Zapata

(10) Patent No.: US 6,214,984 B1
(45) Date of Patent: Apr. 10, 2001

(54) ISOLATED NUCLEIC ACID ENCODING, AND METHODS FOR PREPARING, ANTIBODY FRAGMENTS

(75) Inventor: Gerardo A. Zapata, Berwyn, PA (US)

(73) Assignee: Genentech, Inc., South San Francisco, CA (US)

(*) Notice: Subject to any disclaimer, the term of this patent is extended or adjusted under 35 U.S.C. 154(b) by 0 days.

(21) Appl. No.: 09/249,230

(22) Filed: Feb. 11, 1999

Related U.S. Application Data

(62) Division of application No. 08/811,757, filed on Mar. 6, 1997, now Pat. No. 6,066,719, which is a continuation of application No. 08/425,763, filed on Apr. 20, 1995, now Pat. No. 5,641,870.

(51) Int. Cl.$^7$ .................................................. C12N 15/13

(52) U.S. Cl. .................. 536/23.4; 536/23.1; 536/23.53; 530/387.3; 435/69.6; 435/69.7; 435/328

(58) Field of Search ........................ 424/133.1; 435/91.1, 435/69.6, 69.7, 328; 530/387.3; 536/23.1, 23.53, 23.4

(56) References Cited

U.S. PATENT DOCUMENTS

| 4,000,098 | 12/1976 | Hofstee . |
| 5,429,746 | 7/1995 | Shadle et al. . |
| 5,591,828 | 1/1997 | Bosslet et al. . |
| 5,648,237 | 7/1997 | Carter . |

FOREIGN PATENT DOCUMENTS

| 57621/90 | 1/1991 | (AU) . |
| WO 92/12993 | 8/1992 | (WO) . |
| WO 92/22653 | 12/1992 | (WO) . |
| WO 93/11161 | 6/1993 | (WO) . |
| WO 94/13804 | 6/1994 | (WO) . |
| WO 94/13806 | 6/1994 | (WO) . |
| WO 97/14719 | 4/1997 | (WO) . |

OTHER PUBLICATIONS

Abe et al., "Purification of monoclonal antibodies with light–chain heterogeneity produced by mouse hybridomas raised with NS–1 myelomas: application of hydrophobic interaction high–performance liquid chromatography" *Journal of Biochemical and Biophysical Methods* 27:215–227 (1993).

Alfthan et al., "Purification of Labelled Antibodies by Hydrophobic Interaction Chromatography" *J. Chromatography* 470 (385–389):385–389 (1989).

Axelsson K., "Bacterial Lipopolysaccharides and Glutathione Mixed Disulfides as Possible Contaminants of Human Growth Hormone Produced with the Use of *E. coli* K12" *Acta Chemica Scandinavica, Series B* 39(1):69–77 (1985).

Berkowitz et al., "Use of high–performance hydrophobic interaction chromatography for the determination of salting–out conditions of proteins" *Journal of Chromatography* 389:317–321 (1987).

Bridonneau et al., "Behaviour of human immunoglobulin G subclasses on thiophilic gels: comparison with hydrophobic interaction chromatography" *Journal of Chromatography* 616:197–204 (1993).

Bywater et al., "Desorption of Immunoglobulins from Protein A–Sepharose CL–4B under Mild Conditions" *Journal of Immunological Methods* 64:1–6 (1983).

Carter et al., "High level *escherichia coli* expression and production of a bivalent humanized antibody fragment" *Bio/Technology* 10:163–167 (1992).

Cruse et al. *Illustrated Dictionary of Immunology*, CRC Press, Inc. pp. 18–19, 107–109 (1995).

Danielsson et al., "One–step purification of monoclonal IgG antibodies from mouse ascites" *Journal of Immunological Methods* 115:79–88 (1988).

Eigenbrot et al., "X–Ray Structures of Fragments From Binding and Nonbinding Versions of a Humanized Anti–CD18 Antibody: Structural Indications of the Key Role of $V_H$ Residues 59 to 65" *Proteins: Structure, Function, and Genetics* 18:49–62 (1994).

Fausnaugh et al., "Solute and Mobil Phase Contributions to Retention in Hydrophobic Interaction Chromatography of Proteins" *J. Chromatography* 359:131–146 (1986).

Fendly et al., "The Extracellular Domain of HER2/neu Is a Potential Immunogen for Active Specific Immunotherapy of Breast Cancer" *Journal of Biological Response Modifiers* 9:449–455 (1990).

Gagnon et al., "Method Development and Scale–Up in the Purification of Monoclonal Antibodies by Ion Exchange and Hydrophobic Interaction Chromatography" *Abstract of the Annual Meeting* (Abstract No. 0–4) (May 13, 1990).

Hildreth et al., "A Human Lymphocyte–associated Antigen Involved in Cell–mediated Lympholysis" *European Journal of Immunology* 13:202–208 (1983).

Holliger et al., "Diabodies: Small bivalent and bispecific antibody fragments" *Proc. Natl. Acad. Sci. USA* 90:6444–6448 (Jul. 1993).

Hudziak et al., "p185$^{HER2}$ Monoclonal Antibody Has Antiproliferative Effects In Vitro and Sensitizes Human Breast Tumor Cells to Tumor Necrosis Factor" *Molecular & Cellular Biology* 9(3):1165–1172 (1989).

(List continued on next page.)

Primary Examiner—Sheela Huff
Assistant Examiner—Larry R. Helms
(74) Attorney, Agent, or Firm—Wendy M. Lee

(57) ABSTRACT

The present application describes nucleic acid encoding, and methods for preparing, an antibody comprising a linear $V_H$—$C_H1$—$V_H$—$C_H1$ heavy chain fragment associated with two light chains.

3 Claims, 9 Drawing Sheets

OTHER PUBLICATIONS

Inouye et al., "Fragmentation of mouse monoclonal antibodies of the immunoglobulin M class into F(ab')$_2$ fragments and the application of the fragments to immunoassays" *Protein Engineering* (Abstract No. 44) pp. 1018–1019 (1993).

Inouye et al., "One–Step Purification of F(ab')$_2$ Fragments of Mouse Monoclonal Antibodies (Immunoglobulins G1 and M) by Hydrophobic Interaction HPLC" *Animal Cell Technology: Basic & Applied Aspects* 5:609–616 (1993).

Inouye et al., "Single–step purification of F(ab')$_{2\mu}$ fragments of mouse monoclonal antibodies (immunoglobulins M) by hydrophobic interaction high–performance liquid chromatography using TSKgel Ether–5PW" *Journal of Biochemical and Biophysical Methods* 26:27–39 (1993).

Johansson et al., "Purification of proteins by salt promoted adsorption chromatography" *Biol. Recombinant Microorg. Anim. Cells* (Oholo 34 Meeting) pp. 409–414 (1991).

Kelley et al., "Antigen Binding thermodynamics and Antiproliferative Effects of Chimeric and Humanized anti–p185HER2 Antibody Fab Fragments" *Biochemistry* 31:5434–5441 (1992).

Kurzban et al., "Purification of Bovine Liver Rhodanese by Low–pH Column Chromatography" *Protein Expression and Purification* 2:279–384 (1991).

Mendelson et al., "Preparation and Characterization of Polyclonal and Monoclonal Antibodies against Human Aromatase Cytochrome P–450 (P–450$_{AROM}$), and Their Use in its Purification" *Archives of Biochemistry & Biophysics* 243(2):480–491 (1985).

Morimoto et al., "Single–step purification of F(ab')$_2$ fragments of mouse monoclonal antibodies (immunoglobulins G1) by hydrophobic interaction high performance liquid chromatography using TSKgel Phenyl–5PW" *Journal of Biochemical and Biophysical Methods* 24:107–117 (1992).

Nardella et al., "Nonimmunospecific Protein–Protein Interactions of IgG: Studies of the Binding of IgG to IgG Immunoadsorbents" *Journal of Immunology* 120(3):739–744 (1978).

Nau et al., "The Role of Hydrophobic Interaction Chromatography in Antibody Purification—Optimization of Mobile Phase Conditions" *BioChromatography* 5(2):62–73 (1990).

Neblock et al., "Conjugation and Evaluation of 7E3 X P4B6, a chemically Cross–Linked Bispecific F9ab')2 Antibody Which Inhibits Platelet Aggregation and Localizes Tissue Plasminogen Activator to the Platelet Surface" *Bioconjugate Chem* 3:126–131 (1992).

Panka et al., "Variable region framework differences result in decreased or increased affinity of variant anti–digoxin antibodies" *Proc. Natl. Acad. Sci. USA* 85:3080–3084 (May 1988).

Paulus, H., "Preparation and Biomedical Applications of Bispecific Antibodies" *Behring Inst. Mitt.* 78:118–132 (1985).

Pavlu et al., "Rapid Purification of Monoclonal Antibodies by High–Performance Liquid Chromatography" *Journal of Chromatography* 359:449–460 (1986).

Rea et al., "The Rapid Development of Hydrophobic Interaction Chromatography Purification of a Murine Monoclonal IgG$_{2a}$ F(ab')$_2$ Fragment" *Journal of Cellular Biochemistry* (Abstract No. X1–206) Suppl.A:pg. 50 (1993).

Regnier, F., "High–Performance Liquid Chromatography of Biopolymers" *Science* 222 (4621):245–252 (1983).

Rodrigues et al., "Development of a Humanized Disultide–stabilized Anti–p185HER2 Fv–B–Lactamase Fusion Protein for Activation of a Cephalosporin Doxorubicin Prodrug" *Cancer Research* 55:63–70 (Jan. 1, 1995).

Rodrigues et al., "Engineering Fab' Fragments for Efficient F(ab)$_2$ Formation in *Escherichia coli* and for Improved In Vivo Stability" *The Journal of Immunology* 151(12):6954–6961 (Dec. 15, 1993).

Rudikoff et al., "Single amino acid substitution altering antigen–binding specificity" *Proc. Natl. Acad. Sci. USA* 79:1979–1983 (1982).

Scopes, "Protein Purification: Principles and Practice" *Springer Advanced Texts in Chemistry,* Springer Advanced Texts in Chemistry pp. 176–181 (1987).

Shaltiel, S., "Hydrophobic Chromatography" *Methods in Enzymology* 104:69–96 (1984).

Williams, G., "Novel antibody reagents: production and potential" *TIBTECH* 6:36–42 (1988).

Young et al., "Staphylococcal Protein A Binding to the Fab Fragments of Mouse Monoclonal Antibodies" *J. of Immunology* 133(6):3163–3166 (Dec. 1984).

Zapata et al., "Engineering linear F(ab')$_2$ fragments for efficient production in *Escherichia coli* and enhanced antiproliferative activity" *Protein Engineering* 8(10):1057–1062 (1995).

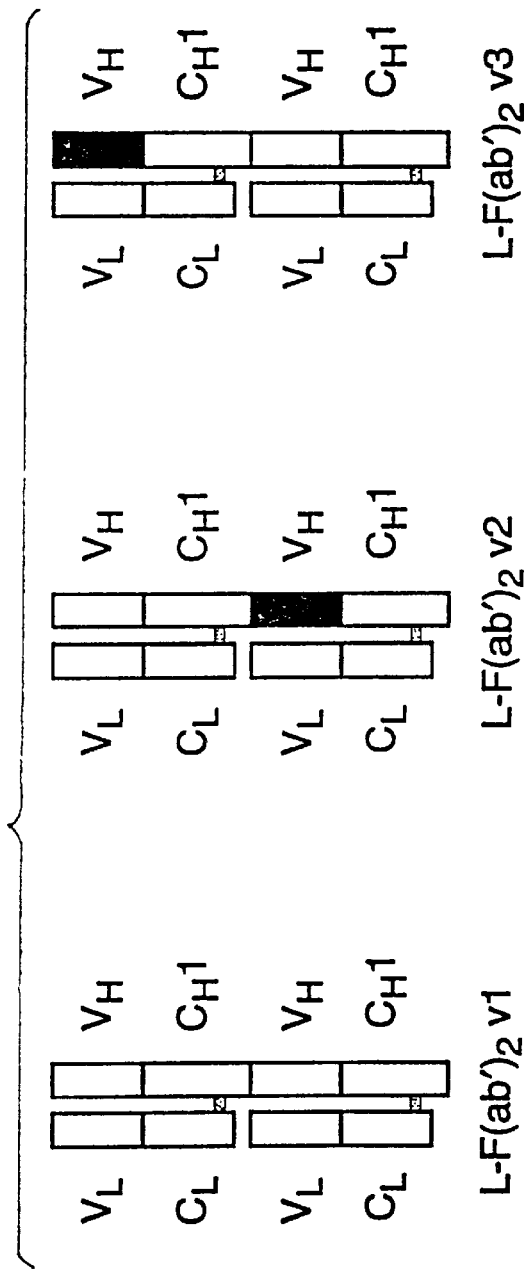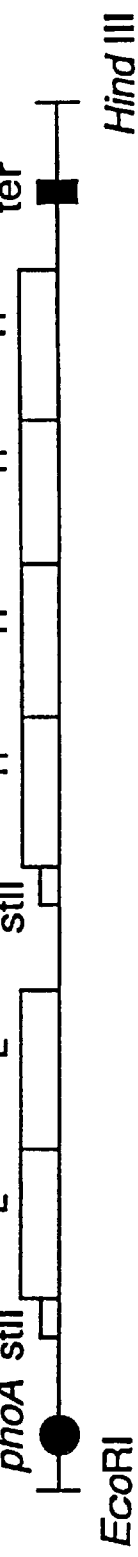
FIG.5A
FIG.5B

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 214 amino acids
      (B) TYPE: amino acid
      (D) TOPOLOGY: linear (xi) SEQUENCE DESCRIPTION: SEQ ID NO: 1:

```
Asp Val Gln Met Thr Gln Thr Thr Ser Ser Leu Ser Ala Ser Leu
 1               5                  10                  15

Gly Asp Arg Val Thr Ile Asn Cys Arg Ala Ser Gln Asp Ile Asn
                20                  25                  30

Asn Tyr Leu Asn Trp Tyr Gln Gln Lys Pro Asn Gly Thr Val Lys
                35                  40                  45

Leu Leu Ile Tyr Tyr Thr Ser Thr Leu His Ser Gly Val Pro Ser
                50                  55                  60

Arg Phe Ser Gly Ser Gly Ser Gly Thr Asp Tyr Ser Leu Thr Ile
                65                  70                  75

Ser Asn Leu Asp Gln Glu Asp Ile Ala Thr Tyr Phe Cys Gln Gln
                80                  85                  90

Gly Asn Thr Leu Pro Pro Thr Phe Gly Gly Thr Lys Leu Glu
                95                 100                 105

Ile Arg Arg Ala Val Ala Ala Pro Ser Val Phe Ile Phe Pro Pro
               110                 115                 120

Ser Asp Glu Gln Leu Lys Ser Gly Thr Ala Ser Val Val Cys Leu
               125                 130                 135

Leu Asn Asn Phe Tyr Pro Arg Glu Ala Lys Val Gln Trp Lys Val
               140                 145                 150

Asp Asn Ala Leu Gln Ser Gly Asn Ser Gln Glu Ser Val Thr Glu
```

```
                        155                 160                 165
Gln Asp Ser Lys Asp Ser Thr Tyr Ser Leu Ser Ser Thr Leu Thr
                    170                 175                 180

Leu Ser Lys Ala Asp Tyr Glu Lys His Lys Val Tyr Ala Cys Glu
                    185                 190                 195

Val Thr His Gln Gly Leu Ser Ser Pro Val Thr Lys Ser Phe Asn
                    200                 205                 210

Arg Gly Glu Cys
            214

(2) INFORMATION FOR SEQ ID NO: 2:

(i) SEQUENCE CHARACTERISTICS:
        (A) LENGTH: 232 amino acids
        (B) TYPE: amino acid
        (D) TOPOLOGY: linear (xi) SEQUENCE DESCRIPTION: SEQ ID NO: 2:

Glu Val Gln Leu Gln Gln Ser Gly Pro Glu Leu Val Lys Pro Gly
  1               5                  10                  15

Ala Ser Val Lys Ile Ser Cys Lys Thr Ser Gly Tyr Thr Phe Thr
                    20                  25                  30

Glu Tyr Thr Met His Trp Met Lys Gln Ser His Gly Lys Ser Leu
                    35                  40                  45

Glu Trp Ile Gly Gly Phe Asn Pro Lys Asn Gly Gly Ser Ser His
                    50                  55                  60

Asn Gln Arg Phe Met Asp Lys Ala Thr Leu Ala Val Asp Lys Ser
                    65                  70                  75

Thr Ser Thr Ala Tyr Met Glu Leu Arg Ser Leu Thr Ser Glu Asp
                    80                  85                  90

Ser Gly Ile Tyr Tyr Cys Ala Arg Trp Arg Gly Leu Asn Tyr Gly
                    95                 100                 105

Phe Asp Val Arg Tyr Phe Asp Val Trp Gly Ala Gly Thr Thr Val
                   110                 115                 120

Thr Val Ser Ser Ala Ser Thr Lys Gly Pro Ser Val Phe Pro Leu
                   125                 130                 135

Ala Pro Ser Ser Lys Ser Thr Ser Gly Gly Thr Ala Ala Leu Gly
                   140                 145                 150

Cys Leu Val Lys Asp Tyr Phe Pro Glu Pro Val Thr Val Ser Trp
                   155                 160                 165

Asn Ser Gly Ala Leu Thr Ser Gly Val His Thr Phe Pro Ala Val
                   170                 175                 180

Leu Gln Ser Ser Gly Leu Tyr Ser Leu Ser Ser Val Val Thr Val
                   185                 190                 195

Pro Ser Ser Ser Leu Gly Thr Gln Thr Tyr Ile Cys Asn Val Asn
                   200                 205                 210

His Lys Pro Ser Asn Thr Lys Val Asp Lys Lys Val Glu Pro Lys
                   215                 220                 225

Ser Cys Asp Lys Thr His Thr
                   230     232
```

ISOLATED NUCLEIC ACID ENCODING, AND METHODS FOR PREPARING, ANTIBODY FRAGMENTS

This application is a divisional of application Ser. No. 08/811,757 filed on Mar. 6, 1997 (now U.S. Pat. No. 6,066,719), which is a continuation of application Ser. No. 08/425,763 filed on Apr. 20, 1995 (now U.S. Pat. No. 5,641,870), which applications are incorporated herein by reference and to which applications priority is claimed under 35 USC §120.

BACKGROUND OF THE INVENTION

1. Field of the Invention

This invention relates to nucleic acid encoding, and methods for preparing, an antibody comprising a linear $V_H$—$C_H1$—$V_H$—$C_H1$ heavy chain fragment associated with two chains.

2. Description of Related Art

Hydrophobic interaction chromatography (HIC) is a useful tool for separating molecules based on their hydrophobicity. Generally, sample molecules in a high salt buffer are loaded on the HIC column. The salt in the buffer interacts with water molecules to reduce tne solvation of the molecules in solution, thereby exposing hydrophobic regions in the sample molecules which are consequently adsorbed by the HIC column. The more hydrophobic the molecule, the less salt needed to promote binding. Usually, a decreasing salt gradient is used to elute samples from the column. As the ionic strength decreases, the exposure of the hydrophilic regions of the molecules increases and molecules elute from the column in order of increasing hydrophobicity. Sample elution may also be achieved by the addition of mild organic modifiers or detergents to the elution buffer. HIC is reviewed in *Protein Purification,* 2d Ed., Springer-Verlag, New York, pgs 176–179 (1988).

HIC has been used by various researchers for purification of antibodies. Danielsson et al., *Journal of Immunological Methods* 115:79–88 (1988) found that HIC was particularly useful for purification of monoclonal antibodies from mouse ascites when the isoelectric point of the antibodies was below 7.2. HIC was performed with an Alkyl SUPEROSE HR™ column. The buffer system was 0.1 M phosphate, with addition of ammonium sulfate. Usually the starting buffer contained 2 M ammonium sulfate. Bridonneau et al. *Journal of Chromatography* 616:197–204 (1993) were interested in determining whether or not different HIC columns could be used for selective purification of human immunoglobulin G (IgG) subclasses. The antibodies were adsorbed on Phenyl-, Butyl-, or Octyl-SEPHAROSE™ columns in 1 M ammonium sulfate (pH 7.0) and eluted with decreasing salt gradient. Octyl-SEPHAROSE™ medium yielded a poorly adsorbed fraction somewhat enriched in $IgG_{2a}$. See also Berkowitz et al., *Journal of Chromatography* 389:317–321 (1987); Gagnon et al. (90th Annual Meeting, American Society for Microbiology, Anaheim, May 13–17, 1990) Abstract No.0–4; Johansson et al. *Biol. Recombinant Microorg. Anim. Cells,* (Oholo 34 Meeting), 409–414 (1991); Pavlu et al., *Journal of Chromatography* 359:449–460 (1986) and Abe et al., *Journal of Biochemical and Biophysical Methods* 27:215–227 (1993) concerning HIC of antibodies.

HIC has also been used for purifying antibody fragments. Inouye et al., *Protein Engineering,* pgs 6, 8 and 1018–1019 (1993); Inouye et al., *Animal Cell Technology: Basic & Applied Aspects* 5:609–616 (1993); Inouye et al., *Journal of Biochemical and Biophysical Methods* 26:27–39 (1993) and Morimoto et al., *Journal of Biochemical and Biophysical Methods* 24:107–117 (1992) prepared $F(ab')_2$ fragments from pepsin digests of mouse IgM monoclonal antibodies using a TSKgel Ether-5PW™ HIC column. The antibody fragments were salted out with 60% ammonium sulfate and the precipitates were dissolved into phosphate-buffered saline (PBS, pH7.4) containing 1 M ammonium sulfate. This solution was loaded onto the HIC column which had been equilibrated with PBS also containing 1 M ammonium sulfate. The $F(ab')_2$ fragments which were adsorbed onto the column were eluted by reducing the ammonium sulfate concentration in the elution buffer to 0 M. Inouye et al., found that the fraction containing the $F(ab')_2$ was homogeneous by both SDS-PAGE and gel filtration HPLC. The method was considered to be suitable for large-scale purification of $F(ab')_2$ fragments. Similarly, Rea et al.,*Journal of Cell. Biochem.* Suppl. 0, Abstract No. X1-206 (17 Part A), p. 50 (1993) evaluated HIC for purification of a $F(ab')_2$ fragment produced by peptic digestion of a murine $IgG_{2a}$ monoclonal antibody. Protein A purification for removal of residual intact antibody preceded the HIC step. The purification performance of three different HIC columns was tested at several different salts and pHs. POROS PE™ (Phenyl ether) was found to be the best column and phosphate-buffered sodium sulfate at pH 8 gave the best resolution of the $F(ab')_2$ fragment.

SUMMARY OF THE INVENTION

In contrast to the above described HIC techniques, which are generally performed at about neutral pH in the presence of high salt concentrations (using a salt gradient to elute the antibody), the instant invention relates to low pH hydrophobic interaction chromatography (LPHIC) for antibody purification. Preferably, the LPHIC is performed at low salt concentrations, i.e., about 0–0.25 M salt, preferably about 0–0.1 M salt and more preferably 0–50 mM salt. This low salt concentration also applies to the loading buffer. Preferably, no salt gradient is used to elute the antibody.

In particular, the invention provides a process for purifying an antibody from a contaminant which comprises loading a mixture containing the antibody and the contaminant on a hydrophobic interaction chromatography column and eluting the antibody from the column with a buffer having a pH of about 2.5–4.5. Preferably the buffer is at a pH of about 2.8–3.5 and more preferably at a pH of about 3.1. Usually, the mixture loaded onto the column is at about the same pH as the elution buffer.

The method is particularly useful for purifying antibody fragments, especially correctly folded and disulfide linked antibody fragments (e.g. Fab fragments) from contaminating antibody fragments which are not correctly folded and/or disulfide linked. The invention resides, at least in part, in the identification of a problem associated with the formation of recombinant immunoglobulins. It has been observed that such production results in the formation of functional $F(ab')_2$ antibodies as well as a variety of incorrectly associated light and heavy fragments. The most difficult impurity to remove has been characterized herein as a correctly folded antibody fragment whose light and heavy chains fail to associate through disulfide bonding. This antibody impurity can be detected by SDS PAGE gels and Reverse Phase HPLC as heavy and light chains. The LPHIC described herein provides a means for substantially removing this contaminant from partially purified compositions derived from host cells producing the recombinant antibody fragment, although it is not limited to purification of recombinant products.

The invention also relates to the antibody formulation prepared by the process and uses for this antibody formulation.

BRIEF DESCRIPTION OF THE DRAWINGS

FIG. 3A depicts near-UV spectra of rhuMAb H52OZG2 and FIG. 3B depicts far-UV spectra of rhuMAb H52OZG2. This antibody is a mutant of rhuMAb H52OZG1 in which cysteine residues 214 and 227, involved in disulfide bonding between the heavy and light chains, were mutated to serine residues. Circular dichroism spectra in both the far and near UV regions showed a transition point around pH 3.2 (thick line). A transition point represents a change from folded antibody fragment, to its unfolded state. FIG. 3C is a near-UV spectra of rhuMAb H52OZG1 and FIG. 3D is a far-UV spectra of rhuMAb H52OZG1. This antibody fragment showed a different transition point at pH 2.5 (thick line).

FIGS. 5A and 5B depict L-F(ab')$_2$ design and expression cassette described in Example 2 herein. FIG. 5A is a schematic representation of L-F(ab')$_2$ variants (v1, v2 and v3) in which variable (V) domains from the anti-p185$^{HER2}$ Ab, huMAb4D5-8, and from the anti-CD18 Ab, huMAb H52OZG1, are denoted by open and filled boxes, respectively. FIG. 5B is a schematic representation of the dicistronic operon for expression of anti-p185$^{HER2}$ L-F(ab')$_2$ variants derived from plasmid pAK19. Expression is under the transcriptional control of the E. coli alkaline phosphatase promoter (phoA) which is inducible by phosphate starvation. Each antibody (Ab) chain is preceded by the E. coli heat-stable enterotoxin ll (stll) signal sequence to direct secretion to the periplasmic space of E. coli. The humanized $V_L$ and $V_H$ (both copies) domains are precisely fused on their 3' side to human $\kappa_1$ $C_L$ and $IgG_1$ $C_H 1$ constant domains, respectively. The H chain comprises tandemly duplicated segments in which the 5' $C_H 1$ domain is joined in frame to a $V_H$ encoding segment. The 3' $C_H 1$ domain is followed by the bacteriophage lambda $t_0$ transcriptional terminator (ter).

FIG. 6A shows L-F(ab')$_2$ v1; FIG. 6B shows thioether linked F(ab')$_2$; and FIG. 6C shows Fab titration with p185$^{HER2}$ extracellular domain (ECD).

Figure 1:
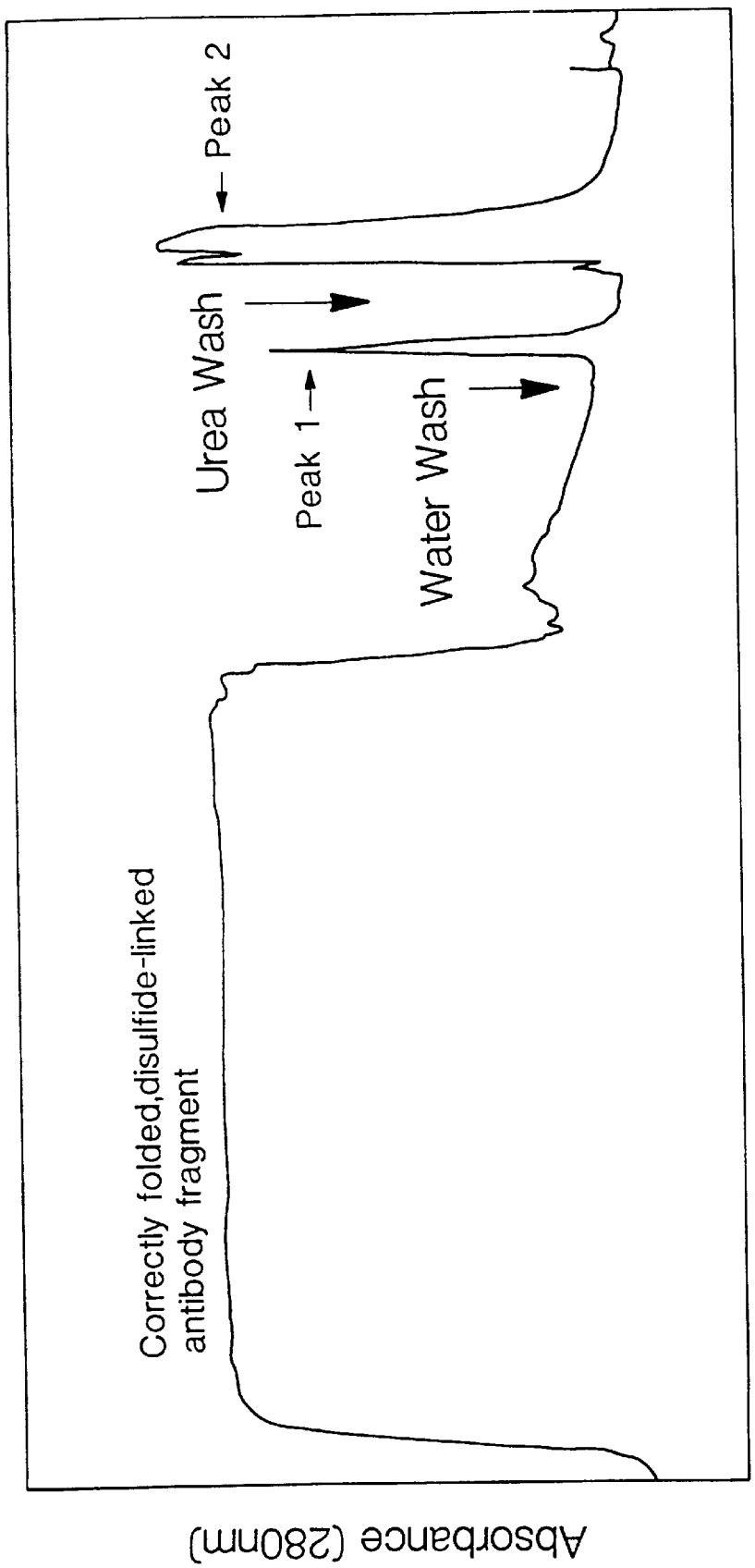
FIG. 1 shows a typical flow through chromatogram of low pH hydrophobic interaction chromatography (see Example 1). The column was operated in the flow-through mode. Correctly folded, disulfide linked antibody fragment flows through. Light chain, heavy chain, light-heavy aggregates and non disulfide linked antibody fragment species remain attached to the column. Peak 1 is the flow-through following water wash, peak 2 is the urea wash of the bound species.

$$C_t = 155 e^{-1.73t} + 190 e^{-0.042t}, L\text{-}F(ab')_2 v1;$$

$$C_t = 239 e^{-0.704t} + 38.4 e^{-0.264t}, F(ab')_2;$$

$$C_t = 440 e^{-4.99t} + 2.69 e^{-0.0442t}, Fab.$$

DETAILED DESCRIPTION OF THE PREFERRED EMBODIMENTS

Definitions:

The term "antibody" is used in the broadest sense and specifically covers intact monoclonal antibodies (including agonist and antagonist antibodies), polyclonal antibodies, multispecific antibodies (e.g. bispecific antibodies) formed from at least two intact antibodies, and antibody fragments so long as they exhibit the desired biological activity.

"Antibody fragments" comprise a portion of an intact antibody, generally the antigen binding or variable region of the intact antibody. Examples of antibody fragments include Fab, Fab', F(ab')$_2$, and Fv fragments; diabodies; linear antibodies (see Example 2 below); single-chain antibody molecules; and multispecific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, Nature, 256:495 (1975), or may be made by recombinant DNA methods (see, e.g., U.S. Pat. No. 4,816,567 [Cabilly et al.]). The "monoclonal antibodies" may also be isolated from phage antibody libraries using the techniques described in Clackson et al., *Nature,* 352:624–628 (1991) and Marks et al., *J. Mol. Biol.,* 222:581–597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (Cabilly et al., supra; Morrison et al., *Proc. Natl. Acad. Sci. USA,* 81:6851–6855 [1984]).

"Humanized" forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework residues of the human immunoglobulin are replaced by corresponding non-human residues. Furthermore, humanized antibodies may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details see: Jones et al., *Nature,* 321:522–525 (1986); Reichmann et al., *Nature,* 332:323–329 (1988); and Presta, *Curr. Op. Struct. Biol.,* 2:593–596 (1992). The humanized antibody includes a Primatized™ antibody wherein the antigen-binding region of the antibody is derived from an antibody produced by immunizing macaque monkeys with the antigen of interest.

The term "diabodies" refers to small antibody fragments with two antigen-binding sites, which fragments comprise a heavy-chain variable domain ($V_H$) connected to a light-chain variable domain ($V_L$) on the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Holliger et al., *Proc. Natl. Acad. Sci. USA,* 90:6444–6448 (1993).

As used herein, "buffer" refers to a buffered solution that resists changes in pH by the action of its acid-base conjugate components. The buffer for the hydrophobic interaction chromatography aspect of this invention has a pH in a range of about 2.5–4.5, preferably about 2.8–3.5. Examples of buffers that will control the pH within this range include phosphate, acetate, citrate or ammonium buffers, or more than one. The preferred such buffers are citrate and ammonium buffers, most preferably ammonium sulfate or ammonium citrate buffers. The "loading buffer" is that which is used to load the mixture of the antibody and contaminant on the HIC column and the "elution buffer" is that which is used to elute the antibody from the column. Often the loading buffer and elution buffer will be the same.

By "correctly disulfide linked" is meant that all cysteine residues in the antibody are covalently associated as disulfide bonds and these disulfide associations correspond to the disulfide associations of the native immunoglobulin. Circular dichroism as described in Example 1 may be used to determine whether or not an antibody is correctly disulfide linked by following the structural integrity of the molecule upon acid denaturation. An antibody is "incorrectly disulfide linked" when one or more cysteine residues are not covalently associated as disulfide bonds or are covalently associated with cysteine residues with which they are normally not associated in the native immunoglobulin.

MODES FOR CARRYING OUT THE INVENTION

The process herein involves purifying an antibody from its related variants, usually after the antibody has already been purified from most other impurities. This purification step may be the final one before therapeutic formulation or it may be followed by other purification step(s). While the antibody in the mixture of variants may be produced from any source (e.g. peptic cleavage of intact antibodies), preferably it is made recombinantly. Techniques for production of antibodies, including antibody fragments, follow.

1. Antibody Preparation (i) Polyclonal antibodies

Polyclonal antibodies are generally raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining 1 mg or 1 μg of the peptide or conjugate (for rabbits or mice, respectively) with 3 volumes of Freund's complete adjuvant and injecting the solution intradermally at multiple sites. One month later the animals are boosted with ⅕ to ⅒ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(ii) Monoclonal antibodies

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

For example, the monoclonal antibodies may be made using the hybridoma method first described by Kohler and Milstein, *Nature*, 256:495 (1975), or may be made by recombinant DNA methods (Cabilly et al., supra).

In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59–103 [Academic Press, 1986]).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 [1984]; Brodeur et al., *Monoclonal Antibody Production Techniques and Applications*, pp. 51–63 [Marcel Dekker, Inc., New York, 1987]).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson and Pollard, *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, supra). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-SEPHAROSE™, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. Review articles on recombinant expression in bacteria of DNA encoding the antibody include Skerra et al., *Curr. Opinion in Immunol.*, 5:256–262 (1993) and Plückthun, *Immunol. Revs.*, 130:151–188 (1992).

In a further embodiment, antibodies or antibody fragments can be isolated from antibody phage libraries generated using the techniques described in McCafferty et al., *Nature*, 348:552–554 (1990), using the proper antigen such as CD11a, CD18, IgE, or HER-2 to select for a suitable antibody or antibody fragment. Clackson et al., *Nature*, 352:624–628 (1991) and Marks et al., *J. Mol. Biol.*, 222:581–597 (1991) describe the isolation of murine and human antibodies, respectively, using phage libraries. Subsequent publications describe the production of high affinity (nM range) human antibodies by chain shuffling (Mark et al., *Bio/Technology*, 10:779–783 [1992]), as well as combinatorial infection and in vivo recombination as a strategy for constructing very large phage libraries (Waterhouse et al., *Nuc. Acids. Res.*, 21:2265–2266 [1993]). Thus, these techniques are viable alternatives to traditional monoclonal antibody hybridoma techniques for isolation of "monoclonal" antibodies.

The DNA also may be modified, for example, by substituting the coding sequence for human heavy- and light-chain constant domains in place of the homologous murine sequences (Cabilly et al., supra; Morrison, et al., *Proc. Nat. Acad. Sci.*, 81:6851 [1984]), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate.

For diagnostic applications, the variants herein derived from antibodies typically will be labeled with a detectable moiety. The detectable moiety can be any one which is capable of producing, either directly or indirectly, a detectable signal. For example, the detectable moiety may be a radioisotope, such as $^3H$, $^{14}C$, $^{32}P$, $^{35}S$, or $^{125}I$; a fluorescent or chemiluminescent compound, such as fluorescein isothiocyanate, rhodamine, or luciferin; radioactive isotopic labels, such as, e.g., $^{125}I$, $^{32}P$, $^{14}C$, or $^3H$; or an enzyme, such as alkaline phosphatase, beta-galactosidase, or horseradish peroxidase.

Any method known in the art for separately conjugating the polypeptide variant to the detectable moiety may be employed, including those methods described by Hunter et al., *Nature*, 144:945 (1962); David et al., *Biochemistry*, 13:1014 (1974); Pain et al., *J. Immunol. Meth.*, 40:219 (1981); and Nygren, *J. Histochem. and Cytochem.*, 30:407 (1982).

(iii) Humanized and human antibodies

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321:522–525 [1986]; Riechmann et al., *Nature*, 332:323–327 [1988]; Verhoeyen et al., *Science*, 239:1534–1536 [1988]), by substituting rodent CDRs or CDR sequences for the corresponding sequences of a human antibody. Accordingly, such "humanized" antibodies are chimeric antibodies (Cabilly et al., supra), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., *J. Immunol.*, 151:2296 [1993]; Chothia and Lesk, *J. Mol. Biol.*, 196:901 [1987]). Another method uses a particular framework derived from the consensus sequence of all human antibodies of a particular subgroup of light or heavy chains. The same framework may be used for several different humanized antibodies (Carter et al., *Proc. Natl. Acad. Sci. USA*, 89:4285 [1992]; Presta et al., *J. Immunol.*, 151:2623 [1993]).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA*. 90:2551–255 (1993); Jakobovits et al., *Nature*, 362:255–258 (1993); Bruggermann et al., *Year in Immuno.*, 7:33 (1993). Human antibodies can also be produced in phage-display libraries (Hoogenboom and Winter, *J. Mol. Biol.*, 227:381 [1991]; Marks et al., *J. Mol. Biol.*, 222:581 [1991]).

(iv) Antibody fragments

Various techniques have been developed for the production of antibody fragments. Traditionally, these fragments were derived via proteolytic digestion of intact antibodies (see, e.g., Morimoto et al., *Journal of Biochemical and Biophysical Methods* 24:107–117 [1992] and Brennan et al., *Science*, 229:81 [1985]). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form $F(ab')_2$ fragments (Carter et al., *Bio/Technology* 10:163–167 [1992]). Alternatively, $F(ab')_2$ fragments can be isolated directly from recombinant host cell culture. Other techniques for the production of antibody fragments will be apparent to the skilled practitioner.

(v) Bispecific antibodies

Bispecific antibodies (BsAbs) are antibodies that have binding specificities for at least two different antigens. Bispecific antibodies can be derived from full length antibodies or antibody fragments (e.g. $F(ab')_2$bispecific antibodies).

Methods for making bispecific antibodies are known in the art. Traditional production of full length bispecific antibodies is based on the coexpression of two immunoglobulin heavy chain-light chain pairs, where the two chains have different specificities (Millstein and Cuello, *Nature*, 305:537–539 [1983]). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, published May 13, 1993, and in Traunecker et al., *EMBO J.*, 10:3655–3659 (1991).

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, $C_H2$, and $C_H3$ regions. It is preferred to have the first heavy-chain constant region ($C_H1$) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690 published Mar. 3, 1994. For further details of generating bispecific antibodies see, for example, Suresh et al., *Methods in Enzymology*, 121:210 (1986).

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the BsAb. The BsAbs produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175:217–225 (1992) describe the production of a fully humanized BsAb F(ab')$_2$ molecule. Each Fab' fragment was separately secreted from *E. coli* and subjected to directed chemical coupling in vitro to form the BsAb. The BsAb thus formed was able to bind to cells overexpressing the HER2 receptor and normal human T cells, as well as trigger the lytic activity of human cytotoxic lymphocytes against human breast tumor targets. See also Rodriguez et al., *Int. J. Cancers, (Suppl.)* 7:45–50 (1992).

Various techniques for making and isolating BsAb fragments directly from recombinant cell culture have also been described. For example, bispecific F(ab')$_2$ heterodimers have been produced using leucine zippers. Kostelny et al., *J. Immunol.*, 148(5):1547–1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. The "diabody" technology described by Hollinger et al., *Proc. Natl. Acad. Sci. (USA)*, 90:6444–6448 (1993) has provided an alternative mechanism for making BsAb fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making BsAb fragments by the use of single-chain Fv (sFv) dimers has also been reported. See Gruber et al., *J. Immunol.*, 152:5368 (1994). These researchers designed an antibody which comprised the $V_H$ and $V_L$ domains of a first antibody joined by a 25-amino-acid-residue linker to the $V_H$ and $V_L$ domains of a second antibody. The refolded molecule bound to fluorescein and the T-cell receptor and redirected the lysis of human tumor cells that had fluorescein covalently linked to their surface.

2. Antibody Purification

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al., *Bio/Technology* 10:163–167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells is preferably subjected to at least one purification step prior to LPHIC. Examples of suitable purification steps include hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.* 62:1–13 [1983]). Protein G is recommended for all mouse isotypes and for human γ3 (Guss et al., *EMBO J.* 5:15671575 [1986]). The matrix to which the affinity ligand is attached is most often agarose, but other matrices are available. Mechanically stable matrices such as controlled pore glass or poly (styrenedivinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™, chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminant(s) is subjected to LPHIC. Often, the antibody composition to be purified will be present in a buffer from the previous purification step. However, it may be necessary to add a buffer to the antibody composition prior to the LPHIC step. Many buffers are available and can be selected by routine experimentation. The pH of the mixture comprising the antibody to be purified and at least one contaminant in a loading buffer is adjusted to a pH of about 2.5–4.5 using either an acid or base, depending on the starting pH. Preferably, the loading buffer has a low salt concentration (i.e. less than about 0.25 M salt).

The mixture is loaded on the HIC column. HIC columns normally comprise a base matrix (e.g. cross-linked agarose or synthetic copolymer material) to which hydrobobic ligands (e.g. alkyl or aryl groups) are coupled. The preferred HIC column comprises an agarose resin substituted with phenyl groups (e.g. a Phenyl SEPHAROSE™ column). Many HIC columns are available commercially. Examples include, but are not limited to, Phenyl SEPHAROSE 6 FAST FLOW™ column with low or high substitution (Pharmacia LKB Biotechnology, AB, Sweden); Phenyl SEPHAROSE™ High Performance column (Pharmacia LKB Biotechnology, AB, Sweden); Octyl SEPHAROSE™ High Performance column (Pharmacia LKB Biotechnology, AB, Sweden); FRACTOGEL™ EMD Propyl or FRACTOGEL™ EMD Phenyl columns (E. Merck, Germany); MACRO-PREP™ Methyl or MACRO-PREP™ t-Butyl Supports (Bio-Rad, California); WP HI-Propyl ($C_3$)™ column (J. T. Baker, New Jersey); and TOYOPEARL™ ether, phenyl or butyl columns (TosoHaas, PA).

The antibody is eluted from the column using an elution buffer which is normally the same as the loading buffer. The elution buffer can be selected using routine experimentation. The pH of the elution buffer is between about 2.5–4.5 and has a low salt concentration (i.e. less than about 0.25 M salt). It has been discovered that it is not necessary to use a salt gradient to elute the antibody of interest; the desired product is recovered in the flow through fraction which does not bind significantly to the column.

The LPHIC step provides a way to remove a correctly folded and disulfide bonded antibody from unwanted contaminants (e.g. incorrectly associated light and heavy fragments). In particular, the method provides a means to substantially remove an impurity characterized herein as a correctly folded antibody fragment whose light and heavy chains fail to associate through disulfide bonding. It has been discovered that the antibody composition prepared using the LPHIC described herein is at least 95% pure. Purities of more than 98% have been achieved using the method described in Example 1.

The antibody composition prepared by LPHIC can be further purified as desired using techniques which are well known in the art. Diagnostic or therapeutic formulations of the purified protein can be made by providing the antibody composition in a physiologically acceptable carrier, examples of which are provided below.

To remove contaminants (e.g. unfolded antibody and incorrectly associated light and heavy fragments) from the HIC column so that it can be re-used, a composition including urea (e.g. 6.0 M urea, 1% MES buffer pH 6.0, 4 mM ammonium sulfate) can be flowed through the column.

3. Uses for the Purified Antibody

Many uses for antibodies which have been purified using the disclosed method are contemplated, including diagnostic and therapeutic uses. Various diagnostic and therapeutic uses for antibodies have been reviewed in Goldenberg et al., *Semin. Cancer Biol.* 1(3):217–225 (1990), Beck et al., *Semin. Cancer Biol.* 1(3):181–188 (1990), Niman, *Immunol. Ser.* 53:189–204(1990) and Endo, *Nippon Igaku Hoshasen Gakkai Zasshi* (*Japan*) 50(8):901–909 (1990), for example.

The antibodies described herein can be used in immunoassays, such as enzyme immunoassays. BsAbs are particularly useful for this type of assay; one arm of the BsAb can be designed to bind to a specific epitope on the enzyme so that binding does not cause enzyme inhibition, the other arm of the antibody can be designed to bind to an immobilizing matrix ensuring a high enzyme density at the desired site. Examples of such diagnostic BsAbs include those having specificity for IgG as well as ferritin, and those having binding specificities for horseradish peroxidase (HRP) as well as a hormone, for example.

The antibodies can be designed for use in two-site immunoassays. For example, two antibodies are produced binding to two separate epitopes on the analyte protein; one antibody binds the complex to an insoluble matrix, the other binds an indicator enzyme.

Antibodies can also be used for in vitro or in vivo immunodiagnosis of various diseases such as cancer. To facilitate this diagnostic use, an antibody which binds a tumor associated antigen can be conjugated with a detectable marker (e.g. a chelator which binds a radionuclide). For example, a antibody having specificity for the tumor associated antigen CEA can be used for imaging of colorectal and thryroid carcinomas. The anti-p185$^{HER2}$ antibody disclosed herein can be used for detecting cancers characterized by amplification of the HER2 protooncogene. Other non-therapeutic, diagnostic uses for the antibody will be apparent to the skilled practitioner.

For diagnostic applications, the antibody typically will be labeled directly or indirectly with a detectable moiety. The detectable moiety can be any one which is capable of producing, either directly or indirectly, a detectable signal. For example, the detectable moiety may be a radioisotope, such as $^3$H, $^{14}$C, $^{32}$P, $^{35}$S, or 125I; a fluorescent or chemiluminescent compound, such as fluorescein isothiocyanate, rhodamine, or luciferin; or an enzyme, such as alkaline phosphatase, beta-galactosidase or HRP.

Any method known in the art for separately conjugating the antibody to the detectable moiety may be employed, including those methods described by Hunter et al., *Nature* 144:945 (1962); David et al., *Biochemistry* 13:1014 (1974); Pain et al., *J. Immunol. Meth.* 40:219 (1981); and Nygren, *J. Histochem. and Cytochem.* 30:407 (1982).

The antibodies of the present invention may be employed in any known assay method, such as competitive binding assays, direct and indirect sandwich assays, and immunoprecipitation assays. Zola, *Monoclonal Antibodies: A Manual of Techniques,* pp. 147–158 (CRC Press, Inc., 1987).

Competitive binding assays rely on the ability of a labeled standard to compete with the test sample analyte for binding with a limited amount of antibody. The amount of analyte in the test sample is inversely proportional to the amount of standard that becomes bound to the antibody. To facilitate determining the amount of standard that becomes bound, the antibody generally is insolubilized before or after the competition, so that the standard and analyte that are bound to the antibody may conveniently be separated from the standard and analyte which remain unbound.

BsAbs are particularly useful for sandwich assays which involve the use of two molecules, each capable of binding to a different immunogenic portion, or epitope, of the sample to be detected. In a sandwich assay, the test sample analyte is bound by a first arm of the antibody which is immobilized on a solid support, and thereafter a second arm of the antibody binds to the analyte, thus forming an insoluble three part complex. See, e.g., U.S. Pat. No. 4,376,110. The second arm of the antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

The antibodies also are useful for the affinity purification of an antigen of interest from recombinant cell culture or natural sources.

Therapeutic uses for the antibodies purified using the method described herein are also contemplated. For example, the antibody can be used for redirected cytotoxicity (e.g. to kill tumor cells), as a vaccine adjuvant, for delivering thrombolytic agents to clots, for delivering immunotoxins to tumor cells, for converting enzyme activated prodrugs at a target site (e.g. a tumor), for treating infectious diseases or targeting immune complexes to cell surface receptors. Therapeutic formulations of the antibody are prepared for storage by mixing the antibody having the desired degree of purity with optional physiologically acceptable carriers, excipients, or stabilizers (Remington's Pharmaceutical Sciences, 16th edition, Osol, A., Ed., [1980]), in the form of lyophilized cake or aqueous solutions. Acceptable carriers, excipients or stabilizers are non-toxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

The antibody also may be entrapped in microcapsules prepared, for example, by coacervation techniques or by interfacial polymerization (for example, hydroxymethylcellulose or gelatin-microcapsules and poly-[methylmethacylate] microcapsules, respectively), in colloidal drug delivery systems (for example, liposomes, albumin microspheres, microemulsions, nano-particles and nanocapsules), or in macroemulsions. Such techniques are disclosed in *Remington's Pharmaceutical Sciences,* supra.

The antibody to be used for in vivo administration must be sterile. This is readily accomplished by filtration through sterile filtration membranes, prior to or following lyophilization and reconstitution. The antibody ordinarily will be stored in lyophilized form or in solution.

Therapeutic antibody compositions generally are placed into a container having a sterile access port, for example, an intravenous solution bag or vial having a stopper pierceable by a hypodermic injection needle.

The route of antibody administration is in accord with known methods, e.g., injection or infusion by intravenous, intraperitoneal, intracerebral, intramuscular, intraocular, intraarterial, or intralesional routes, or by sustained release systems as noted below. The antibody is administered continuously by infusion or by bolus injection.

Suitable examples of sustained-release preparations include semipermeable matrices of solid hydrophobic polymers containing the protein, which matrices are in the form of shaped articles, e.g., films, or microcapsules. Examples of sustained-release matrices include polyesters, hydrogels [e.g., poly(2-hydroxyethyl-methacrylate) as described by Langer et al., *J. Biomed. Mater. Res.* 15:167–277 (1981) and Langer, Chem. Tech. 12:98–105 (1982) or poly (vinylalcohol)], polylactides (U.S. Pat. No. 3,773,919, EP 58,481), copolymers of L-glutamic acid and gamma ethyl-L-glutamate (Sidman et al., *Biopolymers* 22:547–556 [1983]), non-degradable ethylene-vinyl acetate (Langer et al., supra), degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid (EP 133,988).

While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for antibody stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Sustained-release antibody compositions also include liposomally entrapped antibody. Liposomes containing the antibody are prepared by methods known per se: DE 3,218,121; Epstein et al., *Proc. Natl. Acad. Sci. USA* 82:3688–3692 (1985); Hwang et al., *Proc. Natl. Acad. Sci. USA* 77:4030–4034 (1980); EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200–800 Angstroms) unilamellar type in which the lipid content is greater than about 30 mol. % cholesterol, the selected proportion being adjusted for the optimal antibody therapy.

An effective amount of antibody to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. A typical daily dosage might range from about 1 µg/kg to up to 10 mg/kg or more, depending on the factors mentioned above. Typically, the clinician will administer antibody until a dosage is reached that achieves the desired effect. The progress of this therapy is easily monitored by conventional assays.

The following examples are offered by way of illustration and not by way of limitation. The disclosures of all citations in the specification are expressly incorporated herein by reference.

EXAMPLE 1

Low pH Hydrophobic Interaction Chromatography (LPHIC)

A method to preferentially unfold non disulfide linked antibody by acid denaturation has been developed. During acid denaturation, intermolecular charge repulsion contributes to unfolding and the extent of unfolding depends on the conditions of acidification as well as protein structure. At low pH, unfolded antibody and incorrectly associated light and heavy fragments can be separated by LPHIC (flow through mode). Unwanted antibody species bind to the column while desired antibody fragments flow through. Impurities can be removed from the column with 6.0 M urea, 1% MES buffer (pH 6.0), 4 mM ammonium sulfate.

The following antibodies were subjected to LPHIC:
(a) humanized anti-CD18 Fab' and F(ab')$_2$;
(b) chimeric anti-CD18 Fab' and F(ab')$_2$;
(c) linear humanized anti-CD18 F(ab')$_2$; and
(d) linear humanized anti-p185$^{HER2}$ F(ab')$_2$.

Material and Methods

Cell Material. Transformed *E. coli* strains were used to produce humanized anti-CD18 Fab'H52, version OZ (rhuMAb H52OZG1) as described in Eigenbrot et al., *Proteins: Structure, Function and Genetics*, 18:49–62 (1994). A chimeric version of anti-CD18 MAb, MHM23 (Hildreth et al., *Eur. J. Immunol.* 13:202–208 [1983]), was prepared having the light chain sequence SEQ ID No. 1 and heavy chain sequence SEQ ID No. 2. The sequences encoding the Fab were subcloned into a vector based upon pAK19 which has previously been described by Carter et al., *Bio/Technology* 10:163–167 (1992). Linear humanized anti-CD18 huMAbH52 and anti-p185$^{HER2}$ huAb4D5-8 F(ab')$_2$ fragments were produced as described in Example 2 below.

Reverse Phase Chromatography Analysis. Reverse Phase chromatography was carried out on a Reverse Phase PLRP-S™ 4.6×50 mm column, 8 mm particle size, (Polymer Laboratories, Shropshire, UK) maintained at 50° C. The proteins were eluted using an increasing linear gradient from 31% Buffer B to 41% Buffer B. Buffer A contained 0.1% trifluoroacetic acid in deionized water, and Buffer B contained 0.1% trifluoroacetic acid in HPLC grade acetonitrile. The flow rate was maintained at 2 ml/min, and the detection wavelength was 214 nm.

Extraction of Fab' antibody fragments from *E. coli* and protection of free sulfhydryl with 4,4-DTP. Antibody fragments were extracted from *E. coli* frozen cell pellets obtained from 10 liter fermentations. Since the cells were completely disrupted, 4,4-dithiodipyridine (4,4-DTP) was added to protect the free cysteine in Fab' antibody fragment engineered to contain a free thiol in the hinge region (anti-CD18 huMAb H52OZG1 and anti-CD18 MAb MHM23). Linear F(ab')$_2$ versions without engineered free cysteines in the hinge region (anti-CD18 huMAbH52 and huMAb4D5-8 linear versions) were extracted without 4,4-DTP as described in Example 2 below.

Extraction. Frozen cell pellets were re-suspended at room temperature in 20 mM MES buffer, pH 6.0 containing 5 mM EDTA and 20 mM 4,4'-DTP previously dissolved in ethanol (3 liters of buffer/kg of cell pellet). The suspended cells were disrupted by two passages through a Mantin Gaulin homogenizer at 5500 to 6500 PSI. The homogenate was adjusted to 0.25% (v/v) with polyethyleneimine (PEI) and diluted with an equal volume of 2–8° C. purified water. The diluted homogenate was then centrifuged. The antibody fragment was found in the supernatant.

Purification of the protected Fab'-TP antibody fragments. ABX™ chromatography was used for the initial purification of the antibody fragments from *E. coli* proteins. To further purify the antibody fragments from antibody species that lack a disulfide bond between the light and heavy chains, a low pH hydrophobic interaction chromatography step was introduced.

ABX™ chromatography. The supernatant containing the antibody fragment was diluted to a conductivity of 2 millisiemens or less with purified water. The diluted is supernatant was pumped sequentially through 0.5 and 0.22 micron filters and loaded onto a ABX™ column (J. T. Baker Phillipsburg, N.J.) equilibrated in 50 mM MES/5 mM EDTA, pH 6.0 (Buffer A). The effluent was monitored at 280 nm. After loading, the column was washed with Buffer A for 2 column volumes. Antibodies were eluted with a 20 column volume gradient from 0 to 50 mM ammonium sulfate in Buffer A. Fractions were analyzed by HPLC and pooled accordingly.

Low pH Hydrophobic Interaction Chromatography (LPHIC). The ABX™ purified Fab' pools (humanized and chimeric anti-CD18) were adjusted to 20 mM NaPO$_4$ and the pH of the pools was adjusted to 3.1 using 6 N HCL immediately prior to loading on a Phenyl SEPHAROSE™ Fast Flow (Pharmacia Biotech Inc. Piscataway, N.J.) column. Chemically coupled F(ab')$_2$ (humanized and chimeric anti-CD18) and linear F(ab')$_2$ (anti-CD18 and anti-p185$^{HER2}$) ABX™ pools were prepared in the same way except that they were made 20 mM in ammonium sulfate. A typical flow through chromatogram of the LPHIC is shown in FIG. 1. The pH of the LPHIC purified antibody was immediately adjusted to pH 5, with 10% NaOH.

pH analysis. An experiment was designed to determine the pH at which maximum purification as well as maximum yield could be achieved. ABX™ pools were made 25 mM in NaPO$_4$ and the pH was adjusted using 6 N HCl. After the desired pH was obtained, the samples were flowed through a Phenyl SEPHAROSE™ Fast Flow column and the pools were analyzed using Reverse Phase HPLC to determine purity and yield.

Circular Dichroism. Spectra was recorded on an AVIV model 60DS instrument at 25° C. Path length cells of 1 mm were used for far UV measurements and 10 mm path length cells for near UV measurements. The rhuMAb H52OZG1 and rhuMAb H52OZG2 purified antibody samples were buffer exchanged into 10 mM KPO$_4$ buffer by gel permeation chromatography on SEPHADEX G25™ (Pharmacia Biotech Inc. Piscataway, N.J.). The samples were titrated with phosphoric acid to desired pH prior to measuring the CD spectra.

Results and Discussion

Figure 2:
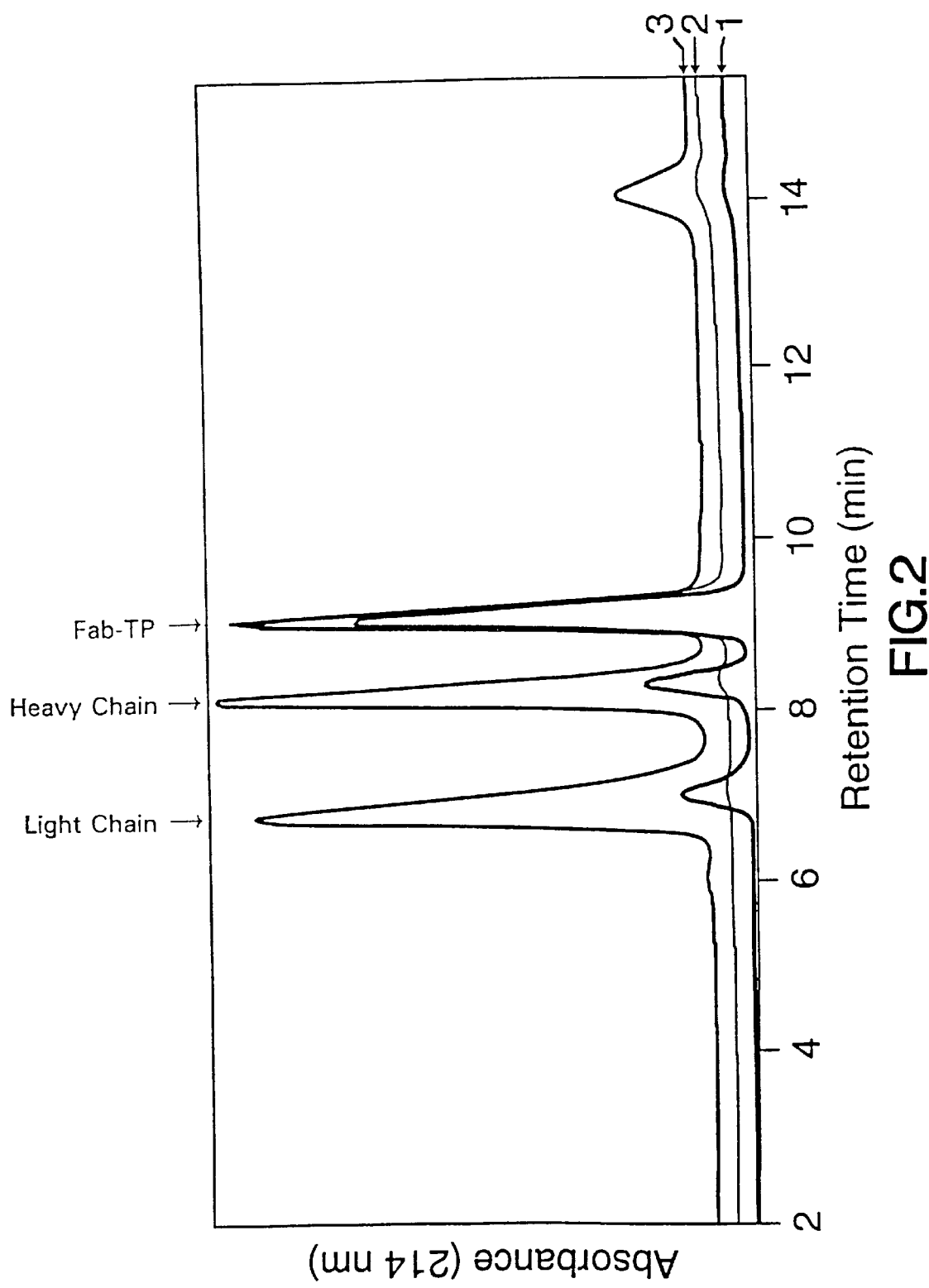
FIG. 2 depicts a Reverse Phase HPLC analysis of ABX™ and Phenyl SEPHAROSE™ Fast Flow (FF) pools of anti-CD18 MHM23 antibody fragment. Chromatogram 1; ABX™ pool containing light and heavy chain contaminants present before LPHIC purification. Chromatogram 2; LPHIC purification. Chromatogram 3; Reverse Phase analysis of the column regeneration buffer containing light and heavy chain impurities and antibody fragments retained by the Phenyl SEPHAROSE™ FAST FLOW column.
Figure 3A:
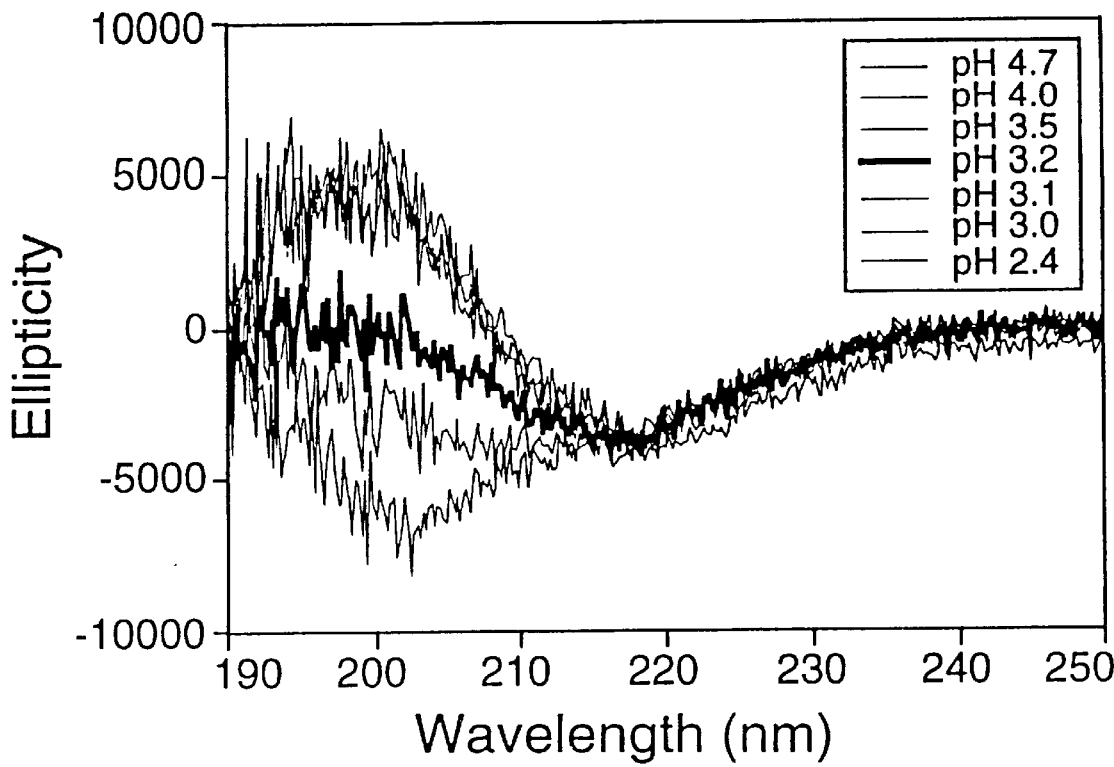
FIGS. 3A–3D depict near UV and far UV spectra of two antibody fragments, rhuMAb H52OZG1 and rhuMAb H52OZG2, obtained by circular dichroism.
Figure 3B:
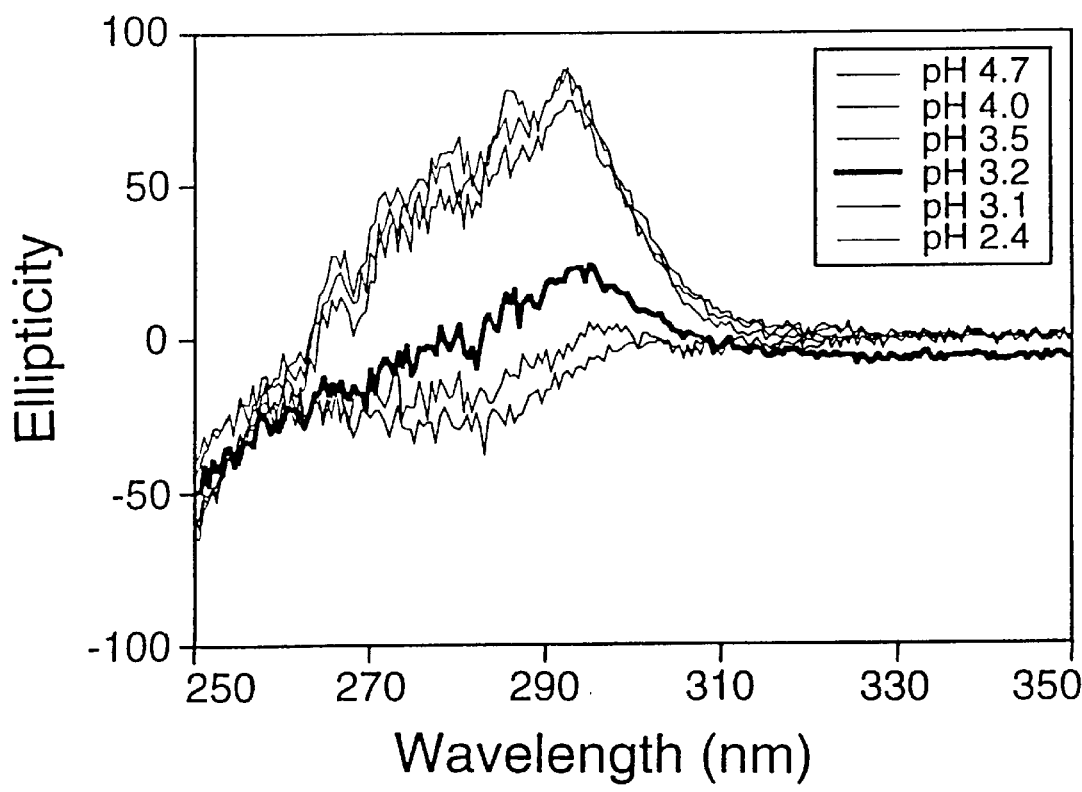
Figure 3C:
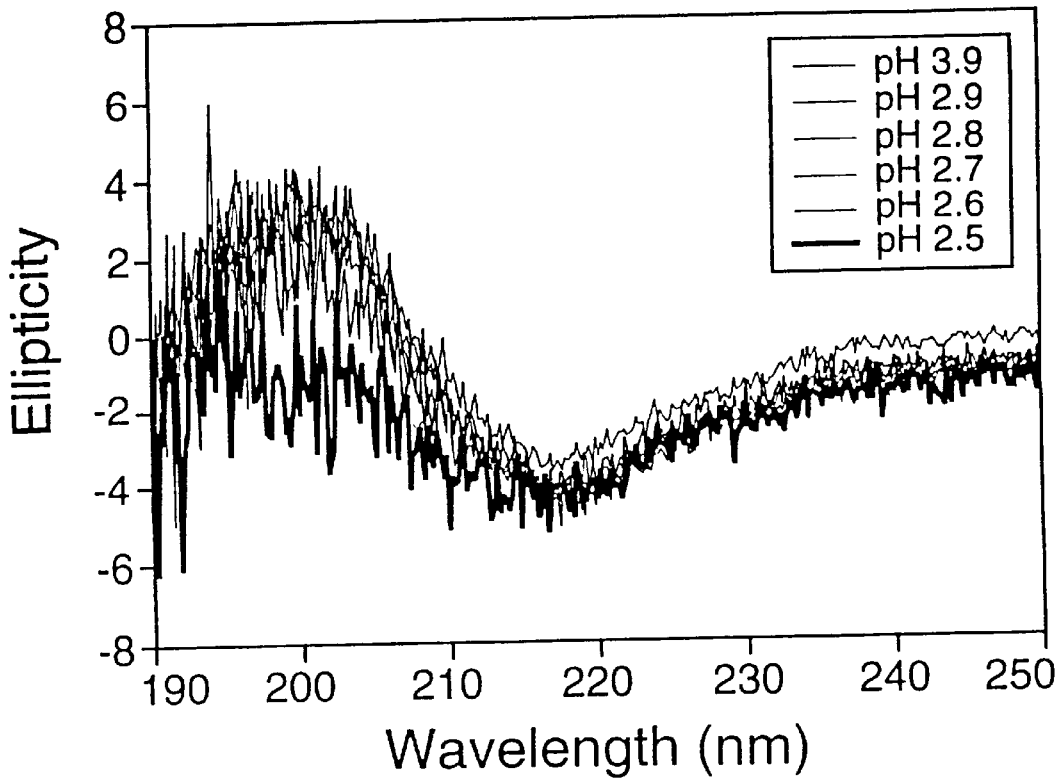
Figure 3D:
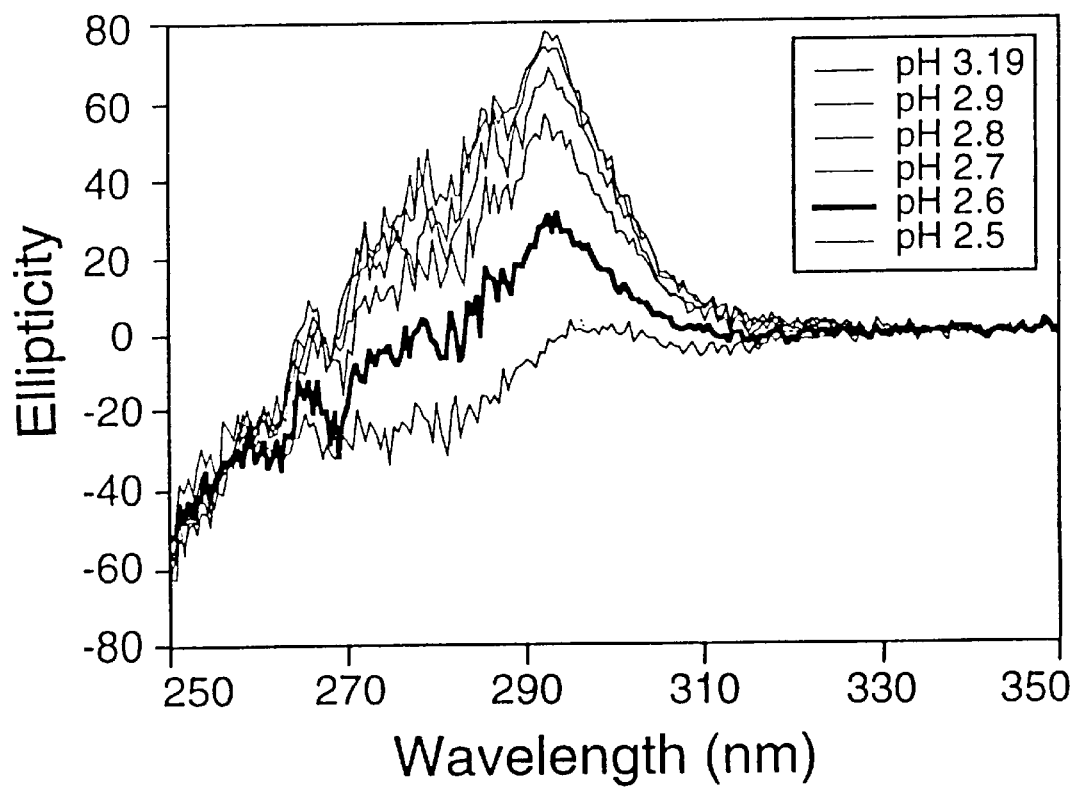

CD Spectroscopy of rhuMAb H52OZG1 and rhuMAb H52OZG2. The ABX™ purified pool appears to contain small amounts of antibody fragments whose light and heavy chains are correctly folded but fail to covalently associate through a disulfide bond. This impurity can be detected on SDS gels and by analytical Reverse Phase HPLC (FIG. 2). The non-covalently associated antibody fragments can be separated from the desired product by preferential acid denaturation followed by LPHIC. To determine the acid denaturation differences between the disulfide associated and non disulfide associated species two purified antibody fragments were used; rhuMAb H52OZG2 and rhuMAb H52OZG1. RhuMAb H52OZG2 is a mutant of rhuMAb H52OZG1 in which the cysteine residues 214 and 227 in the light and the heavy chains respectively have been changed to serine residues. This mutant should mimic the acid denaturation behavior of non disulfide linked antibodies. Near-UV and far-UV spectra of rhuMAb H52OZG2 and rhuMAb H52OZG1 at different pH values show different denaturation transition points (FIGS. 3A–3D). A transition point represents a change from correctly folded antibody fragment, to its unfolded state. Non disulfide associated fragments can be denatured around pH 3.2, whereas the disulfide associated fragments required pH values below 2.5 for denaturation.

Figure 4:
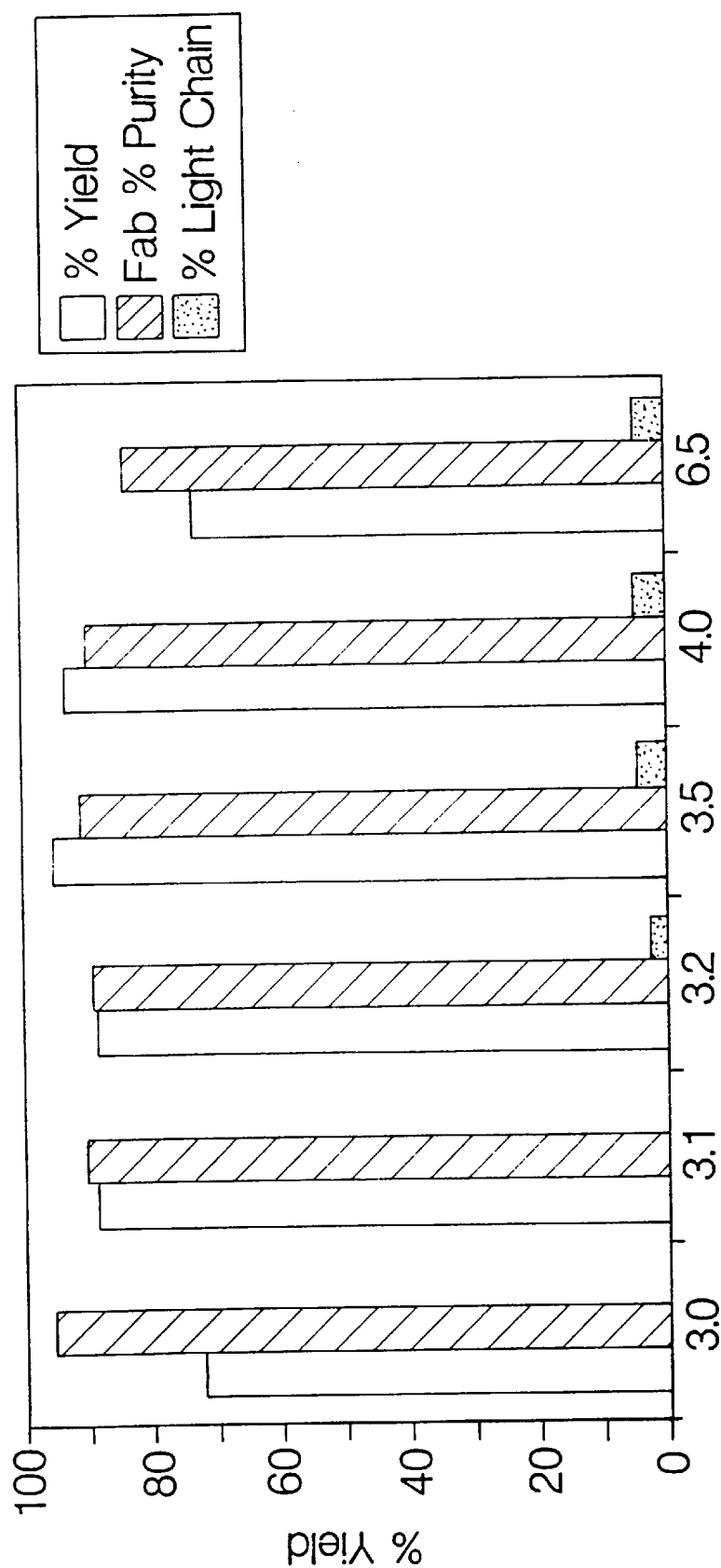
FIG. 4 is a bar graph depicting the consequences on product yield of varying the HIC pH. ABX™ purified antibody fragment pools containing the linkless antibody impurity (i.e. having no disulfide bond between the heavy and light chain) were further purified on a Phenyl SEPHAROSE FAST FLOW™ column. The purification was performed at pH values between 3.0 and 6.5 in order to determine the best pH to obtain maximum yield and purity. Analysis of the flow through pools was performed using Reverse Phase HPLC. From the bar graph it can be seen that pH 3.1 represents the best value to maximize both purity and yield in the purification of rhuMAb H52OZG1 antibody fragment.

LPHIC pH analysis. From the acid denaturation analysis it can be concluded that around pH 3.0 the non disulfide associated fragments can be denatured and then preferentially bound to a Phenyl SEPHAROSE™ Fast Flow column. In order to evaluate the effect of varying low pH's on the LPHIC step, ABX™ purified antibody pools were LPHIC purified at different pH values. Analysis of the purified pools was performed using Reverse Phase HPLC. A bar graph was generated in which purity, yield, and light chain percentages were determined from the LPHIC purifications (FIG. 4). From the bar graph it was determined that pH 3.1 was the best value for balancing purity and yield for the purification of rhuMAb H52OZG1 antibody. Large scale purifications of ABX™ pools were carried out at pH 3.1.

Summary

LPHIC made possible the purification of Fab', L-F(ab')$_2$ and chemically linked F(ab')$_2$ antibody fragments from unwanted antibody species to more than 98% purity. Flow of samples through a Phenyl SEPHAROSE™ Fast Flow column at low pH removed antibodies that lack disulfide bonds between heavy and light chains as well as incorrectly associated light and heavy chain species. Circular Dichroism studies of disulfide linked and non-disulfide linked anti-CD18 F(ab')$_2$ antibodies (rhuMAb H52OZG1 and rhuMAb H52OZG2) demonstrated that the non disulfide linked antibody (rhuMAb H52OZG2) denatured into light and heavy chain molecules at pH 3.2. Disulfide linked antibody (rhuMAb H52OZG1), denatured at pH 2.5. Chromatography experiments at different pH values demonstrated that pH 3.1 represents the best value for balancing purity and yield for purification of anti-CD18 rhuMAb H52OZG1.

EXAMPLE 2

Linear Antibody Production

This example describes the production of bivalent, linear (L-) F(ab')$_2$ fragments (comprising tandem repeats of a heavy chain fragment, $V_H$—$C_H1$—$V_H$—$C_H1$ cosecreted with a light chain) which were subjected to LPHIC (see Example 1 above).

Materials and Methods

Construction of L-F(ab')$_2$ variants. The expression plasmid, pAK19, for secretion of huMAb4D5-8 Fab' fragment has previously been described (Carter et al., *Bio/Technology* 10:163–167 [1992]). Plasmids pLA1, pLA2 and pLA3 were designed to secrete L-F(ab')$_2$ variants v1, v2 and v3, respectively (FIG. 5A). Plasmid pLA1 was constructed from pAK1 9 by modifying the heavy chain to encode tandem huMAb4D5-8 Fd segments: $V_H$—$C_H1$—$V_H$—$C_H1$. L-F(ab')$_2$ v2 and v3 were constructed from pLA1 by precisely replacing 5' or 3' copies of $V_H$ in pLA1, respectively, with that from the humanized anti-CD18 Ab, huMAb H52OZ (Eigenbrot et al., supra). A plasmid was designed to secrete L-F(ab')$_2$ anti-CD18. A plasmid was constructed from anti-CD18 Ab, huMAb H52OZ (Eigenbrot et al., supra) by modifying the heavy chain to encode tandem Fd segments $V_H$—$C_H1$—$V_H$—$C_H1$.

E. coli expression and purification of L-F(ab')$_2$ variants. The production of huMAb4D5-8 Fab and thioether-linked F(ab')$_2$ fragments from *E. coli* has previously been described by Kelley et al., *Biochemistry* 31:5434–5441 (1992) and Rodriguez et al., *J. Immunol.* 151:6954–6961 (1993). L-F (ab')$_2$ variants were secreted from *E. coli* strain 33B6 (Rodriguez et al., *Cancer Res.* 55:63–70 ([1995]) containing corresponding expression plasmids grown for 40 h at 30° C. in an aerated 10 liter fermentor as previously described (Carter et al., supra). Expression titers were estimated by antigen (Ag)-binding ELISA (Carter et al., supra). L-F(ab')$_2$ variants were purified from 400 g of corresponding fermentation pastes thawed in the presence of 2 liters 20 mM MES, 5 mM EDTA, pH 6.0 (ME buffer). Resuspended cells were disrupted by three passages through a microfluidizer (Microfluidics Corporation, Newton, Mass.) and adjusted to 0.25% (v/v) polyethyleneimine. Solid debris was removed by centrifugation (7,300 g, 30 min, 4° C.). The supernatant was diluted with an equal volume of distilled water and then loaded onto a 20 ml Bakerbond ABX™ column (J. T. Baker, Phillipsburg, N.J.) pre-equilibrated with ME buffer. L-F (ab')$_2$ was eluted using a linear gradient of 0–50 mM (NH$_4$SO$_4$ in ME buffer. Pooled L-F(ab')$_2$ was adjusted to 25 mM Na$_2$HPO$_4$, pH 3.0 and passed over a 20 ml Phenyl SEPHAROSE FAST FLOW™ column (high sub) (Pharmacia, Piscataway, N.J.) equilibrated with 25 mM Na$_2$HPO$_4$, 20 mM (NH$_4$)$_2$SO$_4$, pH 3.0. The flow through fractions containing L-F(ab')$_2$ were pooled and adjusted to pH 6.0.

All antibody fragments were buffer-exchanged into PBS by S100-HR™ (Pharmacia) size exclusion chromatography (2.5 cm×100 cm). Residual endotoxin was removed by repeated passage through PYROBIND-ST™ filters (Sepracor, Marlborough, Mass.). The endotoxin level of each preparation was estimated by the limulus amebocyte lysate test (Associates of Cape Cod Inc., Woods Hole, Mass.). The purified antibody (Ab) fragments were passed through a 0.2 mm filter, flash-frozen in liquid nitrogen, and stored at −70° C. until required.

Analysis of Ab fragment binding to p185$^{HER2}$ECD. The affinity and kinetics of binding of huMAb4D5-8 Ab fragments to p185$^{HER2}$ ECD (Fendly et al., *J. Biol. Resp. Mod.* 9:449–455 [1990]) were determined by surface plasmon resonance using the BIAcore system (Pharmacia) as previously described by Kelley and O'Connell in *Biochemistry,* 32:6828–6835 (1993). The stoichiometry of binding of Ab fragments to Ag was determined in solution. Briefly, varying amounts of p185$^{HER2}$ ECD (Fendly et al., supra) in PBS were added to a fixed quantity of Ab fragment (15–20 mg) and the mixture then analyzed by size exclusion FPLC using a SUPEROSE 12™ column (Pharmacia) equilibrated with 0.1 M NaH$_2$HPO$_4$, pH 6.7.

Cell proliferation assay. The effect of huMAb4D5-8 Ab fragments (0–30 mg/ml) upon the proliferation of the human mammary adenocarcinoma cell line, BT474, was investigated as previously described (Hudziak et al., *Molec. Cell. Biol.,* 9:1165–1172 [1989]).

Pharmacokinetics of Ab fragments in normal mice. Groups of female CD-1 mice (20–32 g, n=45) from Hanlen Sprague Dawley (Indianapolis, Ind.) received one of the huMAb4D5-8 Ab fragments (3–4 mg/ml in PBS) by rapid tail vein injection (10 mg/kg). Three mice per time point were sacrificed at scheduled times ranging from 1 min to 24 h post injection, and samples of their serum were collected and stored frozen. Serum concentrations of each Ab fragment were determined by Ag-binding ELISA as previously described using corresponding fragments as standards (Rodriguez et al., supra). Only the thioether-linked F(ab')$_2$ was detectable (0.7 mg/ml) at 24 h following injection.

Data from each treatment group were analyzed by fitting a biexponential function, $C(t)=Ae^{-at}+B3^{-bt}$, to the mean values of the serum concentrations at each time point. Exponential components were estimated by a non-linear least squares method using the Gauss-Newton-Marquardt-Levenberg procedure (Press et al., In *Numerical Recipies in C*, Cambridge University Press, Cambridge, UK, [1988]) and a weighing of $y^{-2}$, where y is the measured serum concentration. Initial volume of distribution ($V_1$), volume of distribution at steady state ($V_{ss}$), clearance time (CL), plus initial and terminal half-lives ($t_{1/2}$) were then calculated from the estimated parameters as described (Wagner, *J. Pharmacokin. Biopharm.* 4:443–467 [1976]):

$$C_0 = A + B$$

$$V_1 = Dose/C_0$$

$$V_{ss} = (A/a^2 + B/b^2)/(AUC)^2$$

$$CL = Dose/AUC$$

$$\text{Initial } t_{1/2} = \ln 2/a$$

$$\text{Terminal } t_{1/2} = \ln 2/b$$

where $C_0$ is the extrapolated initial concentration, and AUC is the area under the fitted plasma concentration versus time curve. The permanence time (T), which is the expected interval of time spent by the drug in all its passages through a compartment (in this case, serum) was estimated (Mordenti and Rescigno, *Pharm. Res.*, 9:17–25 [1992]) as follows:

$$T = AUC/C_0.$$

Results and Discussion

Design of L-F(ab')$_2$. L-F(ab')$_2$ variants were designed to comprise a heavy (H) chain of tandem Fd fragments, $V_H$—$C_H$1—$V_H$—$C_H$1, associated with two copies of the corresponding light (L) chain (FIG. 5A). At the Fd—Fd junction, the C-terminus of $C_H$1 (. . . THT) is joined directly to the N-terminus of $V_H$ (EVQ . . . ) without any extraneous linking protein sequences. This was an attempt to minimize the potential risks of immunogenicity and susceptibility to serum proteases in patients. A potential drawback of this strategy of omitting linkers is that accessibility of the C-terminal binding site to antigen (Ag) might be impaired.

The huMAb4D5-8 L-F(ab')$_2$ variant, v1, was designed to have two functional binding sites for the Ag, p185$^{HER2}$ ECD (FIG. 5A). In contrast, huMAb4D5-8 L-F(ab')$_2$ v2 and v3 were designed to have a single Ag binding site. This was accomplished by replacing either 5' or 3' copies of $V_H$ in L-F(ab')$_2$ v1 with that from the anti-CD18 Ab, huMAbH52 OZ (Eigenbrot et al., supra). A Fab comprising the L chain from huMAb4D5-8 and the H chain Fd fragment from huMAbH52 OZ was expressed and purified and found to not bind p185$^{HER2}$ ECD as anticipated.

Production and in vitro characterization of antibody (Ab) fragments. L-F(ab')$_2$ variants were expressed in *E. coli* by cosecretion of the L chain with the tandem H chain Fd fragments from a dicistronic operon (FIG. 5B). Titers of ≧100 mg/l functional (Ag-binding) huMAb4D5-8 L-F (ab')$_2$ were achieved following culturing of *E. coli* containing corresponding expression plasmids to high cell density in the fermentor. L-F(ab')$_2$ were recovered directly from *E. coli* by fully disrupting corresponding fermentation pastes followed by ABX™, low pH hydrophobic interaction, and size exclusion chromatography. The endotoxin concentration was estimated as ≦0.32 endotoxin units per mg of purified protein.

Purified huMAb4D5-8 L-F(ab')$_2$ variants together with F(ab')$_2$ and Fab were analyzed by SDS-PAGE. Under non-reducing conditions the three huMAb4D5-8 L-F(ab')$_2$ variants ($M_r$~96 kDa) and the Fab fragment ($M_r$~48 kDa) show one major band with the anticipated electrophoretic mobility. The thioether-linked F(ab')$_2$ fragment ($M_r$~96 kDa) shows anomalously retarded mobility as compared to the 97 kDa standard.

Under reducing conditions all huMAb4D5-8 Ab fragments give rise to a band of ~23 kDa apparent molecular weight anticipated for free L chain. In addition, L-F(ab')$_2$ and F(ab')$_2$ give rise to a band of ~48 kDa as anticipated from the presence of tandem and thioether-linked H chain dimers, respectively. The reduced H and L chains for the Fab fragment are not resolved under the electrophoretic conditions used.

Figure 6A:
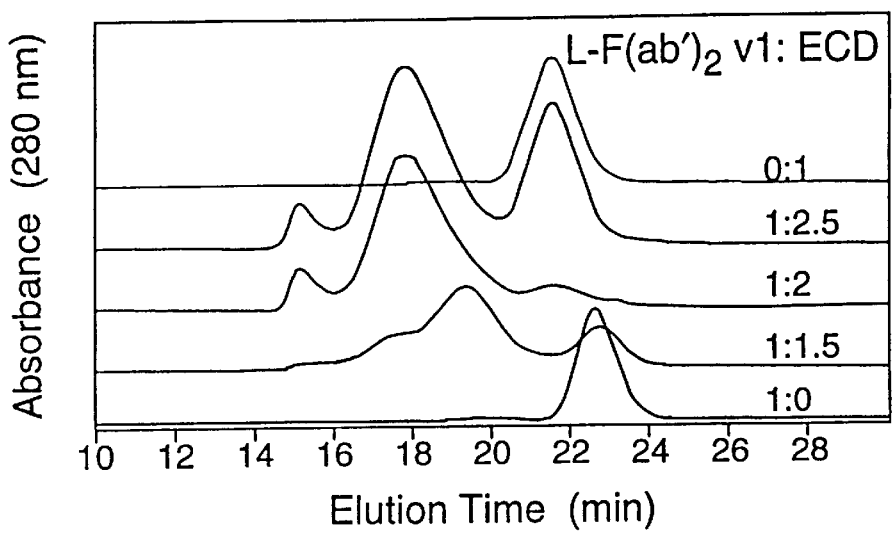
FIGS. 6A–6C depict FPLC size exclusion chromatography analysis of anti-p185$^{HER2}$.
Figure 6B:
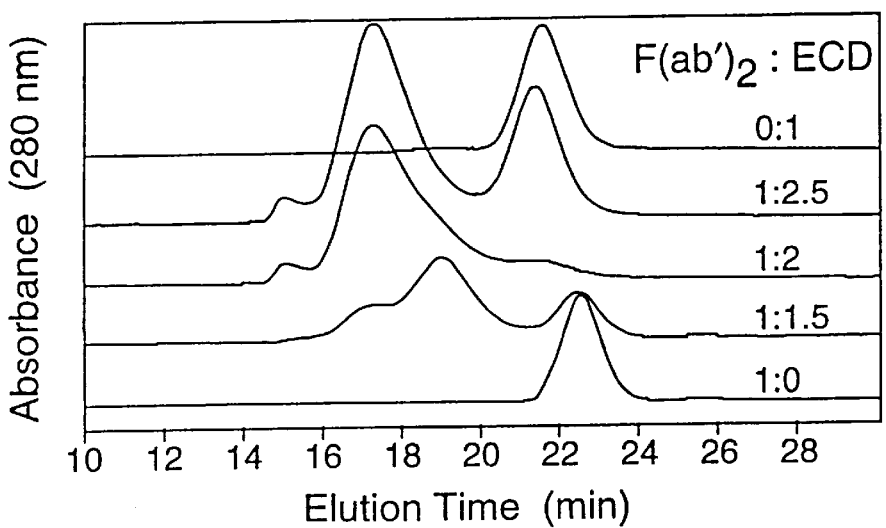
Figure 6C:
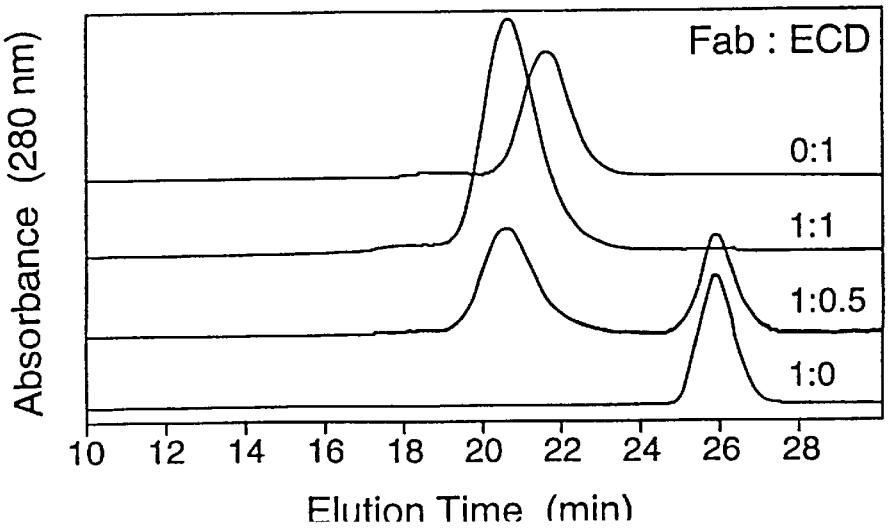

Analysis of binding of Ab fragments to p185$^{HER2}$ECD. The stoichiometry of the Ab–Ag interaction was investigated by titration of huMAb4D5-8 Ab fragments with p185$^{HER2}$ ECD followed by size exclusion chromatographic analysis (FIGS. 6A–6C). huMAb4D5-8 L-F(ab)$_2$ v1 and F(ab')$_2$ show very similar titration profiles with p185$^{HER2}$ ECD and bind two equivalents of antigen (FIGS. 6A and 6B). As anticipated, the Fab fragment binds one equivalent of Ag (FIG. 6C). L-F(ab')$_2$ v2 and v3 bind only a single equivalent of Ag.

The affinity and kinetics of binding of huMAb4D5-8 Ab fragments to Ag were investigated by surface plasmon resonance using immobilized p185$^{HER2}$ ECD. See Table 1 below.

TABLE 1

Binding analysis of anti-p185$^{HER2}$ Ab fragments to p185$^{HER2}$ ECD[a]

| Ab Fragment | $k_{on}$[b] $s^{-1} M^{-1}$ | $k_{off}$[b] $s^{-1}$ | $K_d$ nM |
|---|---|---|---|
| Fab | $3.4 \times 10^5$ | $5.2 \times 10^{-4}$ | 1.5 |
| L-F(ab')$_2$v1 | $6.4 \times 10^5$ | $2.9 \times 10^{-4}$ | 0.46 |
| L-F(ab')$_2$v2 | $2.3 \times 10^5$ | $2.8 \times 10^{-4}$ | 1.2 |
| L-F(ab')$_2$v3 | $5.7 \times 10^5$ | $3.1 \times 10^{-5}$ | 5.5 |
| F(ab')$_2$ | $1.9 \times 10^6$ | $3.2 \times 10^{-4}$ | 0.17 |

[a]Data obtained by surface plasmon resonance.
[b]SE of estimates ≦ ± 3%

The bivalent L-F(ab')$_2$ variant, v1, binds Ag with 3-fold lower affinity than the does F(ab')$_2$. This mainly reflects a small decrease in association rate between F(ab')$_2$ and L-F(ab')$_2$, respectively. The monovalent L-F(ab')$_2$ variants v2 and v3 show approximately 3-fold and 12-fold weaker binding than the bivalent L-F(ab')$_2$ variant, v1. Thus both binding sites in the L-F(ab')$_2$ are competent for binding p$_{185}^{HER2}$ ECD, although the efficiency of Ag binding is apparently slightly impaired for the C-terminal site. As anticipated, the binding affinity of L-F(ab')$_2$ v2 is very similar to the corresponding Fab fragment.

Figure 7:
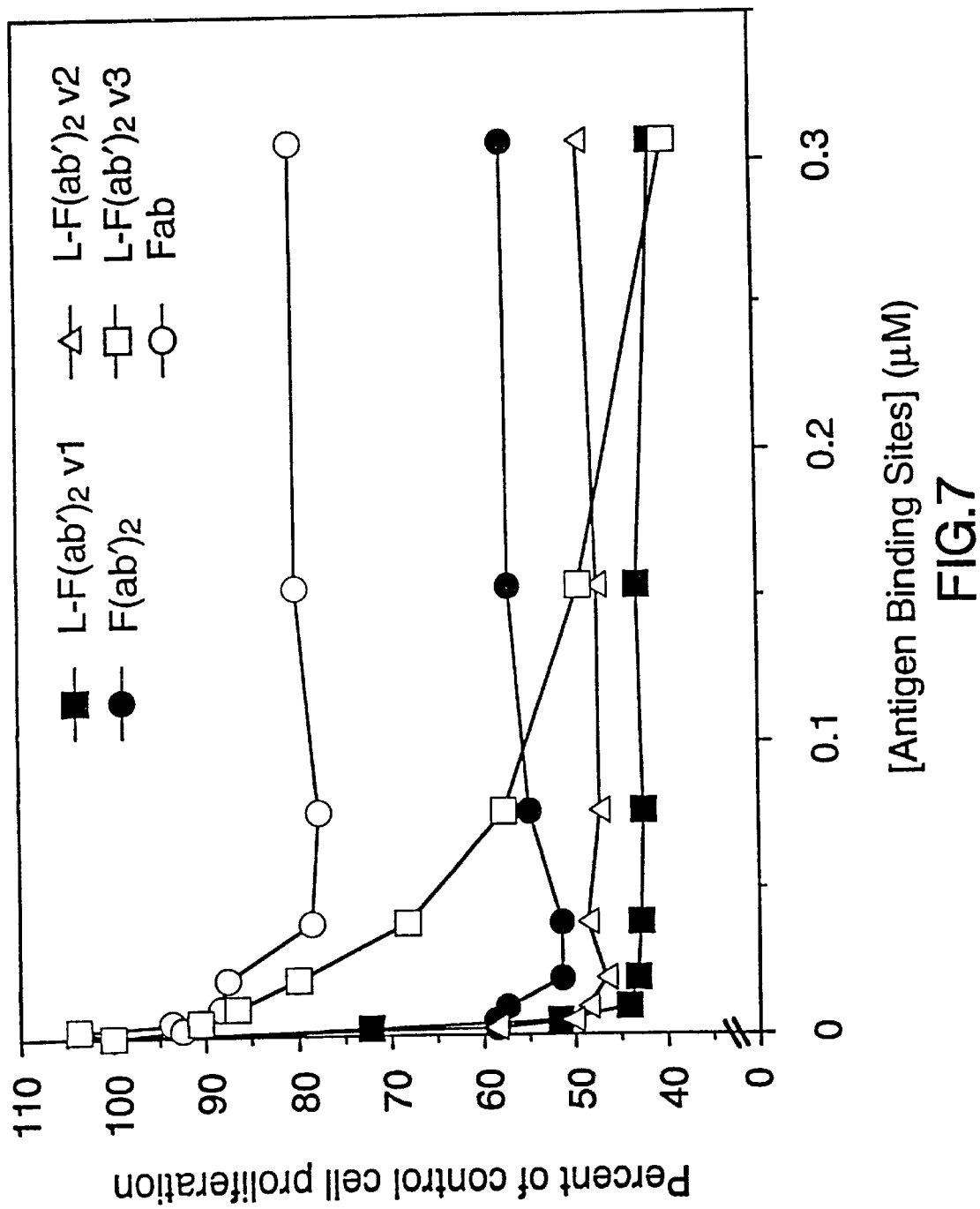
FIG. 7 shows inhibition of proliferation of BT474 cells by anti-p185$^{HER2}$ L-F(ab')$_2$, F(ab')$_2$ and Fab fragments. Data shown are presented as a percentage of results with untreated cultures (mean of duplicate measurements and representative of three separate experiments). Monovalent and bivalent fragments as judged by titration with p185$^{HER2}$ ECD and gel filtration, are represented by open and closed symbols, respectively.

Antiproliferative activity of Ab fragments. The antiproliferative activity of huMAb4D5-8 Ab fragments was investigated using the p185$^{HER2}$-overexpressing breast tumor cell line, BT474 (see FIG. 7). Proliferation of BT474 in the presence of saturating quantities of L-F(ab')$_2$ v1 and thioether-linked F(ab')$_2$ are approximately 40% and 55% of the untreated control, respectively. Thus L-F(ab')$_2$ v1 is more potent in blocking the proliferation of BT474 cells than is the thioether-linked F(ab')$_2$ fragment. The antiproliferative activities of the monovalent L-F(ab')$_2$ variants, v2 and v3, approach that of the bivalent L-F(ab')$_2$ variant, v1, and are much greater than for the Fab fragment.

Figure 8:
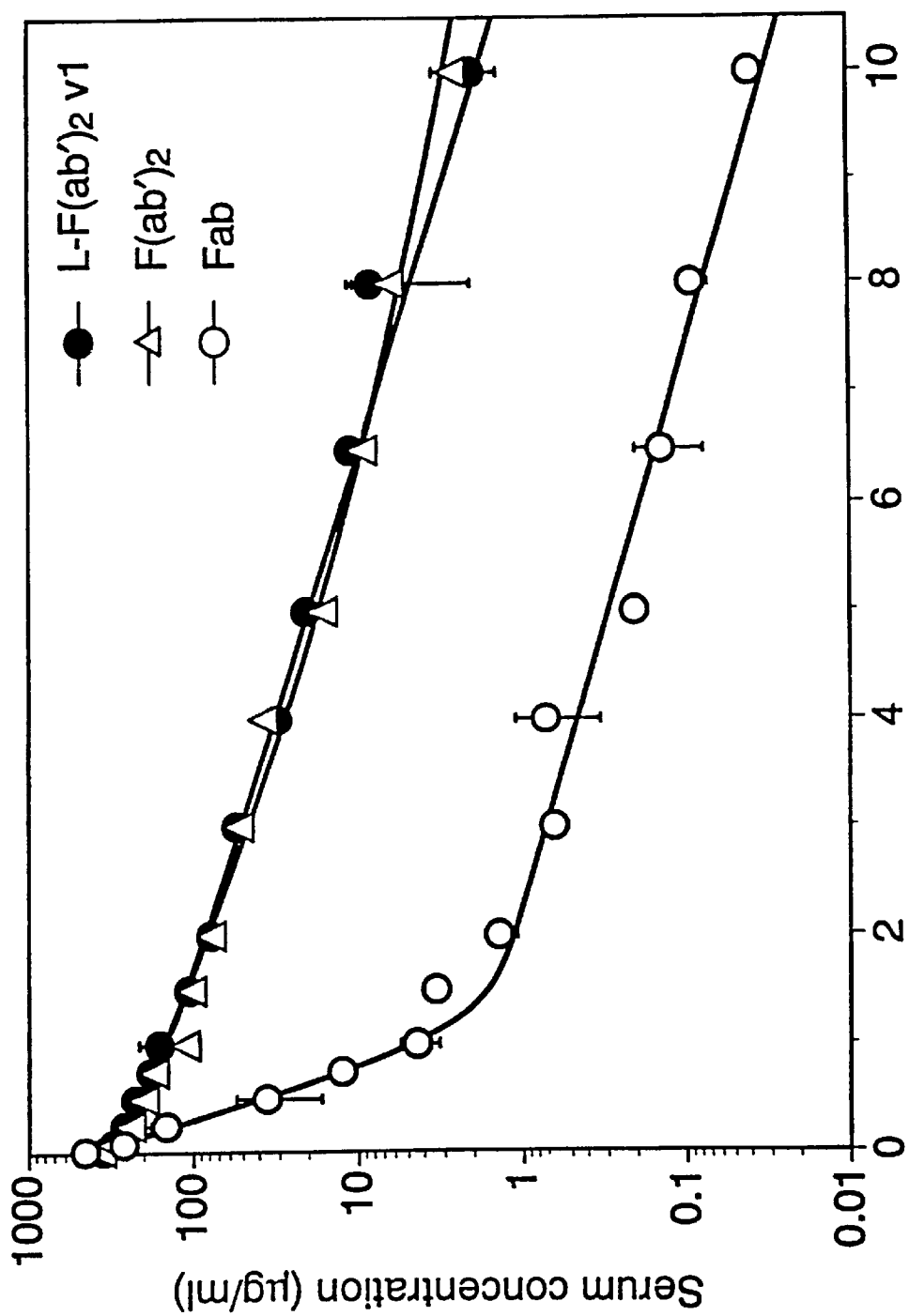
FIG. 8 depicts pharmacokinetics of anti-p185$^{HER2}$ L-F(ab')$_2$v1, Fab and thioether-linked F(ab')$_2$ fragments in normal mice. Serum samples were recovered from groups of 45 female CD-1 mice after a single tail vein injection (10 mg/kg). The mean serum concentrations ($C_t \pm SD$) estimated by antigen (Ag)-binding ELISA are shown together with the non-linear least squares fits (–)

Pharmacokinetic characterization of Ab fragments in normal mice. The time course of huMAb4D5-8 Fab, F(ab')$_2$ and L-F(ab')$_2$ variants in the serum of normal mice was determined from serial sacrifice of multiple animals (FIG. 8) and used for calculation of pharmacokinetic parameters. See Table 2 below.

TABLE 2

Pharmacokinetic parameters for anti-p185$^{HER2}$ Ab fragments in normal mice[a]

| Ab Fragment | $V_1$ ml kg$^{-1}$ | Vss ml kg$^{-1}$ | CL h$^{-1}$ kg$^{-1}$ | t$_½$ hours initial | t$_½$ hours terminal[b] | T hours |
|---|---|---|---|---|---|---|
| L-F(ab')$_2$v1 | 29.0 | 38.0 | 19.3 | 0.40 | 1.6 | 1.50 |
| F(ab')$_2$ | 36.1 | 44.0 | 20.6 | 0.99 | 2.6 | 1.75 |
| Fab | 22.6 | 35.4 | 106 | 0.14 | 1.6 | 0.21 |

[a]Pharmacokinetic parameters were calculated from the data in FIG. 3.
[b]The terminal half-life contributes 83%, 30% and 6.5% to the total AUC for L-F(ab')$_2$v1, F(ab')$_2$ and Fab, respectively.

L-F(ab')$_2$ and thioether-linked F(ab')$_2$ are very similar in terms of their pharmacokinetic parameters, while the Fab fragment is cleared more rapidly. The permanence times in serum for L-F(ab')$_2$ v1 and thioether-linked F(ab')$_2$ fragments, are 7-fold and 8-fold greater than for the Fab fragment, respectively.

What is claimed is:

1. Isolated nucleic acid encoding a linear $V_H$—$C_H1$—$V_H$—$C_H1$ heavy chain fragment, wherein the C-terminus of the first $C_H1$ is joined directly by a peptide bond to the N-terminus of the second $V_H$.

2. The nucleic acid of claim 1 wherein the amino acid sequence of the first $V_H$—$C_H1$ is the same as the amino acid sequence of the second $V_H$—$C_H1$ in the heavy chain fragment.

3. A method for preparing an antibody comprising culturing a host cell comprising the nucleic acid of claim 1 and nucleic acid encoding a light chain which comprises a variable domain, so that the nucleic acids are expressed and recovering the antibody from the host cell culture, wherein the antibody comprises the heavy chain fragment associated with two light chains.

* * * * *